(12) United States Patent
Foitzik et al.

(10) Patent No.: US 10,647,708 B2
(45) Date of Patent: May 12, 2020

(54) TETRAHYDROISOQUINOLINE DERIVED PRMT5-INHIBITORS

(71) Applicant: CTXT PTY LTD, Victoria (AU)

(72) Inventors: Richard Charles Foitzik, Victoria (AU); Michelle Ang Camerino, Victoria (AU); Scott Raymond Walker, Victoria (AU); H. Rachel Lagiakos, Victoria (AU)

(73) Assignee: CTXT PTY. LTD, Victoria (AU)

( * ) Notice: Subject to any disclaimer, the term of this patent is extended or adjusted under 35 U.S.C. 154(b) by 0 days.

(21) Appl. No.: 15/508,063

(22) PCT Filed: Sep. 3, 2015

(86) PCT No.: PCT/EP2015/070155
§ 371 (c)(1),
(2) Date: Mar. 1, 2017

(87) PCT Pub. No.: WO2016/034675
PCT Pub. Date: Mar. 10, 2016

(65) Prior Publication Data
US 2017/0283407 A1 Oct. 5, 2017

(30) Foreign Application Priority Data
Sep. 3, 2014 (GB) .................. 1415573.3

(51) Int. Cl.
| | |
|---|---|
| *C07D 217/04* | (2006.01) |
| *C07D 413/14* | (2006.01) |
| *C07D 401/14* | (2006.01) |
| *C07D 231/12* | (2006.01) |
| *C07D 295/192* | (2006.01) |
| *C07D 239/42* | (2006.01) |
| *C07D 271/10* | (2006.01) |
| *C07D 401/12* | (2006.01) |
| *C07D 405/12* | (2006.01) |
| *C07D 413/12* | (2006.01) |

(52) U.S. Cl.
CPC ......... *C07D 413/14* (2013.01); *C07D 217/04* (2013.01); *C07D 231/12* (2013.01); *C07D 239/42* (2013.01); *C07D 271/10* (2013.01); *C07D 295/192* (2013.01); *C07D 401/12* (2013.01); *C07D 401/14* (2013.01); *C07D 405/12* (2013.01); *C07D 413/12* (2013.01)

(58) Field of Classification Search
CPC .................................................. C07D 217/04
USPC .......................................... 546/146; 514/307
See application file for complete search history.

(56) References Cited

U.S. PATENT DOCUMENTS

| | | | |
|---|---|---|---|
| 6,008,219 A | 12/1999 | Stemp et al. | |
| 6,046,210 A | 4/2000 | Stemp et al. | |
| 6,274,593 B1 | 8/2001 | Johns et al. | |
| 6,579,892 B1 | 6/2003 | Starck et al. | |
| 8,993,555 B2 * | 3/2015 | Duncan | C07D 217/12 514/210.18 |
| 2005/0101647 A1 | 5/2005 | Oda et al. | |
| 2005/0107398 A1 | 5/2005 | Mach et al. | |
| 2006/0235037 A1 | 10/2006 | Purandare | |
| 2010/0069431 A1 | 3/2010 | Iwata et al. | |
| 2015/0344457 A1 * | 12/2015 | Duncan | C07D 401/14 514/210.18 |
| 2016/0222005 A1 | 8/2016 | Stupple et al. | |

FOREIGN PATENT DOCUMENTS

| | | |
|---|---|---|
| CN | 102417483 A | 4/2012 |
| DE | 261153 A1 | 10/1988 |
| GB | 2286395 A | 8/1995 |

(Continued)

OTHER PUBLICATIONS

Golub et al, Science, vol. 286, Oct. 15, 1999, pp. 531-537.*
Pearce et al., Failure modes in anticancer drug discovery and development, Cancer Drug Design and Discovery Edited by Stephen Neidle, Chapter 18, pp. 424-435 (2008).*
Simone, Oncology:Introduction, Cecil Textbook of Medicine, ed Bennett et al. W.B.Saunders Co. 20th ed, vol. 1, 1996, pp. 1004-1010.*
Gura, Systems for identifying New Drugs are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Ouaissi et al., "Rationale for Possible, etc.," Journal of Biomedicine and Biotechnology, 2011, Article: ID 315939, 1-8.*

(Continued)

Primary Examiner — Patricia L Morris
(74) Attorney, Agent, or Firm — Stites & Harbison PLLC; Richard S. Myers, Jr.

(57) ABSTRACT

A compound of formula (I) wherein: $R^1$ is optionally one or more halo or methyl groups; $R^{2a}$ and $R^{2b}$ are independently selected from the group consisting of: (i) F; (ii) H; (iii) Me; and (iv) $CH_2OH$; $R^{2c}$ and $R^{2d}$ are independently selected from the group consisting of: (i) F; (ii) H; (iii) Me; and (iv) $CH_2OH$; $R^{3a}$ and $R^{3b}$ are independently selected from H and Me; $R^4$ is either H or Me; $R^5$ is either H or Me; A is either (i) optionally substituted phenyl; (ii) optionally substituted naphthyl; or (iii) optionally substituted $C_{5-12}$ heteroaryl.

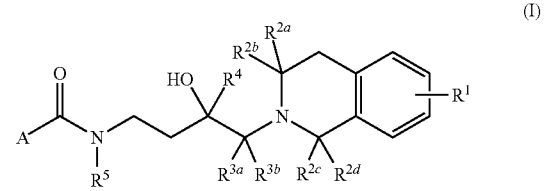

(I)

19 Claims, No Drawings

(56) References Cited

FOREIGN PATENT DOCUMENTS

| WO | WO96/30333 | 10/1996 |
| WO | WO97/43262 A1 | 11/1997 |
| WO | WO98/49145 | 11/1998 |
| WO | WO2003035065 A1 | 5/2003 |
| WO | WO2003082186 A2 | 10/2003 |
| WO | WO2004016611 A1 | 2/2004 |
| WO | WO2004024897 A2 | 3/2004 |
| WO | WO2005030206 A1 | 4/2005 |
| WO | WO2005042495 A1 | 5/2005 |
| WO | WO2006/008133 A2 | 1/2006 |
| WO | WO2006080821 A1 | 8/2006 |
| WO | WO2008061303 A1 | 5/2008 |
| WO | WO2009005551 A2 | 1/2009 |
| WO | WO2009113085 A1 | 9/2009 |
| WO | WO2009139076 A1 | 11/2009 |
| WO | WO2010025295 A2 | 3/2010 |
| WO | WO2012108689 A2 | 8/2012 |
| WO | WO2014100695 A1 | 6/2014 |
| WO | WO2014100716 A1 | 6/2014 |
| WO | WO2014100719 A2 | 6/2014 |
| WO | WO2014100730 A1 | 6/2014 |
| WO | WO2014100734 A1 | 6/2014 |

OTHER PUBLICATIONS

Secci, Daniela et al: "Conventional and microwave-assisted synthesis of benzimidazole derivatives and their in vitro inhibition of human cyclooxygenase", Journal of Heterocyclic Chemistry, 2012, 49(5), 1187-1195.

Rostamizadeh, Shahnaz et al: "Aqueous 1 M Glucose Solution as a Novel and Fully Green Reaction Medium and Catalyst for the Oxidant-Free Synthesis of 2-Arylbenzimidazoles", Synthetic Communications, 2011, 41 (12), 1794-1884.

Chen, Yong-Fei et al: "Design and synthesis of new heterocyclic Bcr-Abl inhibitors", Heterocyclic Comunications, 2010, 16(2-3), 123-135.

Goeker, Hakan et al: "Synthesis and potent antifungal activity against Candida species of some novel 1H-benzimidazoles", Journal of Heterocyclic Chemistry, 2009, 46(5), 936-948.

Kaynak, F. Betul et al: 11 Synthesis and crystal structure of 1-benzyl-2-(4-benzyloxyphenyl)-5,6-dichloro-1H-benzimidazole, Structural Chemistry, 2008, 19(3), 477-488.

Kus, Canan et al: 11 Antimicrobial activity studies on some morpholinobenzimidazole derivatives 11, Ankara Universitesi Eczacilik Fakultesidergisi, 2006, 35(4), 237-244.

K Vijayakumar et al: "Available on line www Synthesis, Anti-Tumor, Anti-Diabetic, and Anti-Asthmatic Activitives of Some Novel Benzimidazole Derivatives", Pharm. Res, vol. 2, No. 4 Jan. 1, 2010 (Jan. 1, 2010), 2010, pp. 215-224.

Richards M L et al: "Substituted 2-phenyl-benzimidazole derivatives: novel compounds that suppress key markers of allergy", European Journal of Medicinal Chemistry, Editions Scientifique Elsevier, Paris, FR, vol. 41, No. 8, Aug. 1, 2006 (Aug. 1, 2006), pp. 950-969.

Zhang, Zeyuan et al: Synthesis and antifungal activity of novel 2,5-disubstituted-1,3,4-oxadiazoles containing benzimidazole moiety, Journal of Pesticide Science (Tokyo, Japan), 2012, 37(4), 338-341.

Aggarwal, et al., Nuclear Cyclin D1/CDK4 Kinase Regulates CUL4 Expression and Triggers Neoplastic Growth via Activation of the PRMT5 Methyltransferase; Cancer Cell, 2010, 18, 329-340.

Berger, Shelley L., Out of the jaws of death: PRMT5 steers p53, nature cell biology vol. 10 | No. 12 | Dec. 2008, pp. 1389-1390.

Gu, et al., Protein arginine methyltransferase 5 is essential for growth of lung cancer cells, Biochemical Journal Immediate Publication. Published on Jun. 18, 2012 as manuscript BJ20120768, pp. 1-20.

Chen, et al., Epigenetic changes during disease progression in a murine model of human chronic lymphocytic leukemia, PNAS, Aug. 11, 2009, vol. 106, No. 32, pp. 13433-13438.

Cho, et al., Arginine methylation controls growth regulation by E2F-1, The EMBO Journal vol. 31 | No. 7 | 2012, pp. 1785-1797.

Durant, et al., p53 methylation, Cell Cycle 8:6, Mar. 15, 2009, pp. 801-802.

He, et al., Induction of human fetal hemoglobin expression by adenosine-2',3'-dialdehyde, Journal of Translational Medicine 2013, 11:14, pp. 1-7.

Jansson, et al., Arginine methylation regulates the p53 response, nature cell biology vol. 10 | No. 12 | Dec. 2008, pp. 1431-1439.

Kanduri, et al., Differential genome-wide array-based methylation profiles in prognostic subsets of chronic lymphocytic leukemia, Blood, Jan. 14, 2010 vol. 115, No. 2, pp. 296-305.

Karkhanis, et al., Versatility of PRMT5-induced methylation in growth control and development, Cell Press, 2011, pp. 1-9.

Kim, et al., Identification of Gastric Cancer-Related Genes Using a cDNA Microarray Containing Novel Expressed Sequence Tags Expressed in Gastric Cancer Cells, Clinical Cancer Research, Jan. 15, 2005, vol. 11, 473-482.

Krause, et al., Protein arginine methyltransferases: Evolution and assessment of their pharmacological and therapeutic potential, Pharmacology & Therapeutics 113 (2007) 50-87.

Le Guezennec, et al., MBD2/NuRD and MBD3/NuRD, Two Distinct Complexes with Different Biochemical and Functional Properties, Molecular and Cellular Biology, Feb. 2006, p. 843-851.

Nicholas, et al., Abstract LB-254: PRMT5 is upregulated in malignant and metastatic melanoma, and regulates expression of the MITF transcription factor, Cancer Res Apr. 15, 2012 72; LB-254.

Pal, et al., mSin3A/Histone Deacetylase 2- and PRMT5-Containing Brg1 Complex Is Involved in Transcriptional Repression of the Myc Target Gene cad, Molecular and Cellular Biology, Nov. 2003, p. 7475-7487.

Pollack, et al., The Human Homologue of the Yeast Proteins Skb1 and Hsl7p Interacts with Jak Kinases and Contains Protein Methyltransferase Activity, J. Biol. Chem. 1999, 274:31531-31542.

Powers, et al., Protein Arginine Methyltransferase 5 Accelerates Tumor Growth by Arginine Methylation of the Tumor Suppressor Programmed Cell Death 4, Cancer Res Published OnlineFirst Jun. 23, 2011, pp. OF1-OF9.

Rank, et al., Identification of a PRMT5-dependent repressor complex linked to silencing of human fetal globin gene expression, Blood, Sep. 2, 2010 vol. 116, No. 9, pp. 1585-1592.

Scoumanne, et al., PRMT5 is required for cell-cycle progression and p53 tumor suppressor function, Nucleic Acids Research, 2009, vol. 37, No. 15 4965-4976.

Pal, et al., Low levels of miR-92b/96 induce PRMT5 translation and H3R8/H4R3 methylation in mantle cell lymphoma, The EMBO Journal (2007) 26, 3558-3569.

Wang, et al., Protein Arginine Methyltransferase 5 Suppresses the Transcription of the RB Family of Tumor Suppressors in Leukemia and Lymphoma Cells, Molecular and Cellular Biology, Oct. 2008, p. 6262-6277.

Gu, et al., Protein Arginine Methyltransferase 5 Functions in Opposite Ways in the Cytoplasm and Nucleus of Prostate cancer Cells, PLOS ONE, Aug. 2012 | vol. 7 | Issue 8, pp. e44033, pp. 1-13.

Mach, et al., Development of Novel 1,2,3,4-Tetrahydroisoquinoline Derivatives and Closely Related Compounds as Potent and Selective Dopamine D3 Receptor Ligands; Chembiochem; 2004; 5; pp. 508-518.

Braun, et al., Ber Dtsch Chem Ges; 1926; pp. 2416-2425.

Zajdel, et al. Solid-Phase Synthesis of Aryl-Alkylamine Derivatives Using Protected Aminoalcohol Building Blocks on SynPhaseTM Lanterns; QSAR Comb. Sci. 26, 2007, No. 2, 215-219.

* cited by examiner

US 10,647,708 B2

TETRAHYDROISOQUINOLINE DERIVED PRMT5-INHIBITORS

The present invention relates to substituted N-alkyl tetrahydroisoquinolines and their use as pharmaceuticals, and in particular, in treating cancer and hemoglobinopathies.

CROSS REFERENCE TO RELATED APPLICATIONS

This application is a § 371 National State Application of PCT/EP2015/070155 filed Sep. 3, 2015 which claims priority to GB 1415573.3 filed Sep. 3, 2014.

BACKGROUND TO THE INVENTION

Post-translational modification of proteins is a hallmark of signal transduction where cells are able to react quickly to changes or events in the cellular environment. Post-translational modification of proteins expands the structural and functional diversity of the proteome. The role of acetylation and phosphorylation of proteins has been extensively studied as highly reversible reactions for fine-tuning responses to external stimuli or changes in the environmental conditions. Recently, the importance of other types of protein modifications, including ubiquitination and methylation has begun to be recognized.

The methylation of proteins and the enzymes that carry out these reactions has increased the dimensions of gene regulation by marking genes that are transcriptionally active or silenced. Protein methylation can occur on amino acids such as lysine, arginine, histidine, or proline, and on carboxy groups.

Arginine methylation of mainly nuclear proteins is an important post-translational modification process involved in structural remodelling of chromatin, signal transduction, cellular proliferation, nucleocytoplasmic shuttling, translation, gene transcription, DNA repair, RNA processing, or mRNA splicing.

Methylation of proteins at arginine residues is catalysed by Protein Arginine Methyltransferase enzymes. The Protein Arginine Methyl Transferase (PRMT) family of enzymes are evolutionarily conserved between organisms but differ in the number of members in different organisms.

There are eleven members of the human PRMT family, eight of which have known enzymatic activity and target substrates. With the exception of PRMT2 and two recently identified putative PRMT genes (PRMT10 and PRMT11), all remaining proteins of the family possess enzymatic arginine methylation activity.

PRMTs are subdivided into two types based on the methylation that they catalyse at the guanidinium group of arginine residues of substrate proteins. There are three nitrogens in the guanidinium group, potentially all of which could be methylated; the two Ψ-guanidino nitrogen atoms and the internal δ-guanidino nitrogen atom. Mono-methylation and dimethylation of arginine (MMA and DMA) is found in mammalian cells at one or both of the two Ψ-guanidino nitrogen atoms; dimethylation may be either symmetric or asymmetric. The third methylated arginine is generated by monomethylation of the internal δ-guanidino nitrogen atom of arginine and has so far been documented only in yeast proteins. Type I PRMT enzymes catalyse the formation of MMA and asymmetric dimethylarginine by di-methylating the same nitrogen atom of the guanidinium group, whereas Type II PRMT enzymes catalyse the formation of MMA and symmetric di-methylarginine by mono-methylating each of the terminal nitrogen atoms. Type III enzymes methylate the internal δ-guanidino nitrogen atom. Of the eight well characterised human PRMTs, PRMT1, 3, 4, 6 and 8 are Type I enzymes, and PRMT5, 7 and 9 are Type II enzymes.

PRMTs catalyse the methylation of the guanidino nitrogen atoms of arginine residues through the transfer of a methyl group from S-adenosyl methionine (SAM). A by-product of the enzymatic methylation step is S-adenosyl-L-homocysteine (AdoHcy), which is hydrolyzed to adenosine and homocysteine by AdoHcy hydrolase (Krause et al., 2007).

PRMT5

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999).

PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

In addition to direct repressive histone marks induced by PRMT5, the enzyme's role in gene silencing is also mediated through the formation of multiprotein repressor complexes that include NuRD components, HDACs, MDB proteins and DNA methyltransferases, (Rank et al., 2010; Le Guezennec et al., 2006; Pal et al., 2003).

PRMT5 is involved in the methylation and functional modulation of the tumour suppressor protein p53. See (Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumour suppression.

p53 target genes have two alternative downstream effects: either they pause the cell cycle, allowing the DNA to be repaired, or, if repair is not possible, they activate processes leading to apoptosis (programmed cell death). How p53 'chooses' between these distinct outcomes is a central question in the field of tumour biology.

p53 is replete with post-translational modifications. Phosphorylation was one of the first post-translational modifications to be clearly defined on p53. In the last decade it has become additionally clear that p53 is modified not only by phosphorylation, but that it is extensively modified by lysine acetylation and methylation, among other modifications. Indeed, besides histone proteins p53 is the most common protein substrate known for these post-translational modifications. However, despite the plethora of post-translational modifications, p53 has not been identified, until recently, as a substrate for arginine methylation.

Jansson et al (Jansson et al., 2008) discovered that PRMT5 is physically associated with a p53 cofactor called Strap. A co-factor complex that contains Strap et al binds to p53 in response to DNA damage. Jansson et al demonstrated that PRMT5 methylates p53 in vitro, and mapped the sites of methylation (R333, R335 and R337). They developed an antibody that specifically detects p53 methylated on these sites and confirmed that p53 is methylated in vivo. Jansson et al went on to show that p53 methylation requires PRMT5 and is increased in response to etoposide, a DNA damaging agent.

The role of PRMT5 and p53 arginine methylation on cell cycle regulation and DNA damage response have been explored by both Jansson et al and Scoumanne et al (Jansson et al., 2008; Scoumanne et al., 2009). Although some differences are evident between the results from the two groups in respect of cell cycle regulation in unperturbed cells (which may be ascribed to cell type specific effects and/or the actual nature of the experimental arrangements), both groups report similar results with respect to the DNA damage response.

In response to DNA damage, caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilisation, decreased basal p53 levels, and decreased p53 oligomerisation, and also decreased expression of eIF4E a major component of translational machinery involved in ribosome binding to mRNA. Indeed, eIF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al showed that a p53 mutant in which each of the three critical arginine residues were substituted with lysine (p53KKK) retained the ability to induce apoptosis but its cell cycle arrest activity was significantly compromised.

Moreover, pS3KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

Taken together, it would seem that PRMT5 is a pro-survival factor, which regulates cell proliferation in unstressed conditions and modulates the p53 response during DNA damage. In particular, knockdown of PRMT5, leading to a reduction in the levels of arginine methylated p53, appears to bias the p53 DNA damage response to proapoptotic as opposed to cell cycle arrest.

PRMT5 is further linked to cancers in that it is aberrantly expressed in around half of human cancer cases. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008).

Moreover, elevated expression of PRMT5 in Melanoma, Breast and Colorectal cancers has been demonstrated to correlate with a poor prognosis.

Lymphoid malignancies including CLL are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al., 2007; Wang et al., 2008). Intriguingly, despite elevated levels of PRMT5 protein in these tumour cells, the levels of PRMT5 mRNA are reduced (by a factor of 2-5). Translation of PRMT5 mRNA is however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumour suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

PRMT5 Function and Hemoqlobinopathies

Hemoglobin is a major protein in red blood cells and is essential for the transport of oxygen from the lungs to the tissues. In adult humans, the most common hemoglobin type is a tetramer called hemaglobin A, consisting of two α and two β subunits. In human infants, the hemaglobin molecule is made up of two α and two γ chains. The gamma chains are gradually replaced by subunits as the infant grows. The developmental switch in human β-like globin gene subtype from foetal (γ) to adult (β) that begins at birth heralds the onset of the hemoglobinopathies β-thalassemia and sickle cell disease (SCD). In β-thalassemia the adult chains are not produced. In SCD a point mutation in the coding sequence in the β globin gene leads to the production of a protein with altered polymerisation properties. The observation that increased adult γ-globin gene expression (in the setting of hereditary persistence of foetal hemoglobin (HPFH) mutations) significantly ameliorates the clinical severity of β-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as β-thalassemia and Sickle Cell Disease (SCD).

The present inventors have developed particular substituted β-hydroxy amides inhibit the activity of PRMT5 and therefore may be of use in treating conditions ameliorated by the inhibition of the activity of PRMT5.

SUMMARY OF THE INVENTION

A first aspect of the present invention provides a compound of formula I:

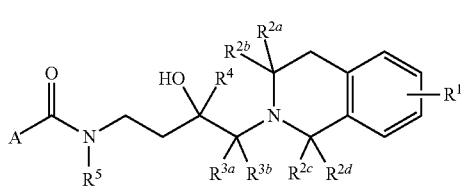

wherein:
  $R^1$ is optionally one or more halo or methyl groups;
  $R^{2a}$ and $R^{2b}$ are independently selected from the group consisting of:
    (i) F;
    (ii) H;
    (iii) Me; and
    (iv) $CH_2OH$;
  $R^{2c}$ and $R^{2d}$ are independently selected from the group consisting of:
    (i) F;
    (ii) H;
    (iii) Me; and
    (iv) $CH_2OH$;
  $R^{3a}$ and $R^{3b}$ are independently selected from H and Me;
  $R^4$ is either H or Me;
  $R^5$ is either H or Me;
  A is either
    (i) optionally substituted phenyl;
    (ii) optionally substituted naphthyl; or
    (iii) optionally substituted $C_{5-12}$ heteroaryl.

A second aspect of the present invention provides a compound of the first aspect for use in a method of therapy. The second aspect also provides a pharmaceutical composition comprising a compound of the first aspect and a pharmaceutically acceptable excipient.

A third aspect of the present invention provides a method of treatment of cancer, comprising administering to a patient in need of treatment, a compound of the first aspect of the invention or a pharmaceutical composition of the first aspect of the invention. The third aspect of the present invention also provides the use of a compound of the first aspect of the invention in the manufacture of a medicament for treating cancer, and a compound of the first aspect of the invention or pharmaceutical composition thereof for use in the treatment of cancer.

As described below, the compound of the first aspect may be administered simultaneously or sequentially with radiotherapy and/or chemotherapy in the treatment of cancer.

A fourth aspect of the present invention provides a method of treatment of hemaglobinopathies, comprising administering to a patient in need of treatment, a compound of the first aspect of the invention or a pharmaceutical composition of the first aspect of the invention. The fourth aspect of the present invention also provides the use of a compound of the first aspect of the invention in the manufacture of a medicament for treating hemaglobinopathies, and a compound of the first aspect of the invention or pharmaceutical composition of the first aspect of the invention for use in the treatment of hemaglobinopathies.

DEFINITIONS $C_{5-12}$ heteroaryl: The term "$C_{5-12}$ heteroaryl" as used herein, pertains to a monovalent moiety obtained by removing a hydrogen atom from an aromatic structure having from 5 to 12 rings atoms, of which from 1 to 3 are ring heteroatoms. The term 'aromatic structure' is used to denote a single ring or fused ring systems having aromatic properties, and the term 'ring heteroatom' refers to a nitrogen, oxygen or sulphur atom.

In this context, the prefixes (e.g. $C_{5-12}$, $C_{5-6}$, etc.) denote the number of atoms making up the aromatic structure, or range of number of atoms making up the aromatic structure, whether carbon atoms or heteroatoms.

Examples of $C_{5-12}$ heteroaryl structures include, but are not limited to, those derived from:
  $N_1$: pyrrole (azole) ($C_5$), pyridine (azine) ($C_6$); pyridone ($C_6$); indole ($C_9$); quinoline ($C_{10}$);
  $O_1$: furan (oxole) ($C_5$);
  $S_1$: thiophene (thiole) ($C_5$);
  $N_1O_1$: oxazole ($C_5$), isoxazole ($C_5$), isoxazine ($C_6$);
  $N_2O_1$: oxadiazole (furazan) ($C_5$);
  $N_1S_1$: thiazole ($C_5$), isothiazole ($C_5$);
  $N_2S_1$: thiadiazole ($C_5$)
  $N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); benzimidazole ($C_9$);
  $N_3$: triazole ($C_5$), triazine ($C_6$).

Optional Substituents

The optional substituents for the phenyl, naphthyl and $C_{5-12}$ heteroaryl groups in A may be selected from the following groups.

$C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

$C_{1-4}$ fluoroalkyl: The term "$C_{1-4}$ fluoroalkyl" refers to a $C_{1-4}$ alkyl group as defined above where one of more of the hydrogen atoms is replaced by a fluoro. Examples of $C_{1-4}$ fluoroalkyl include, but are not limited to, —$CF_3$, $CF_2H$, —$C_2F_5$, and —$C_2F_4H$.

$C_{3-6}$ cycloalkyl: the term '$C_{3-6}$ cycloalkyl' as used herein, pertains to a monovalent moiety obtained by removing a hydrogen atom from a carbon atom of a saturated cyclic core having 4, 5 or 6 atom in the cyclic core all of which are carbon atoms. Examples of $C_{3-6}$ cycloalkyl include, but are not limited to, cyclopropyl, cyclohexyl and cyclopentyl.

$C_{5-6}$ heteroaryl: the term $C_{5-6}$ heteroaryl as used herein, pertains to a monovalent moiety obtained by removing a hydrogen atom from a ring atom of an aromatic structure having between one and three atoms that are not carbon forming part of said ring. Wherein, those atoms that are not carbon can be chosen independently from the list nitrogen, oxygen and sulphur. The group may be substituted by one or more $C_{1-4}$ alkyl groups.

Examples of $C_{5-6}$ heteroaryl groups include, but are not limited to, groups derived from:
$N_1$: pyridine ($C_6$);
$N_1O_1$: oxazole ($C_5$), isoxazole ($C_5$);
$N_2O_1$: oxadiazole (furazan) ($C_5$);
$N_2S_1$: thiadiazole ($C_5$)
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$).

$C_{5-6}$ heteroaryl methyl: —$CH_2$—($C_{5-6}$ heteroaryl), wherein $C_{5-6}$ heteroaryl is as defined above.

$C_{4-6}$ heterocyclyl: The term "$C_{4-5}$ heterocyclyl" as used herein, pertains to a monovalent moiety obtained by removing a hydrogen atom from a ring atom of a monocyclic heterocyclic compound, which moiety has from 4 to 6 ring atoms; of which from 1 to 2 atoms are heteroatoms, chosen from oxygen or nitrogen.

In this context, the prefixes (e.g. $C_{4-6}$) denote the number of ring atoms, or range of number of ring atoms, whether carbon atoms or heteroatoms.

Examples of $C_{4-5}$ heterocyclyl groups include, but are not limited to, those derived from:
$N_1$: azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$N_2$: diazetidine ($C_4$), imidazolidine ($C_5$), pyrazolidine (diazolidine) ($C_5$), imidazoline ($C_5$), pyrazoline (dihydropyrazole) ($C_5$), piperazine ($C_6$);
$O_1$: oxetane ($C_4$), tetrahydrofuran ($C_5$); oxane ($C_6$);
$O_2$: dioxetane ($C_4$), dioxolane ($C_5$); dioxane ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$).

Those $C_{4-6}$ heterocyclyl groups which include a N atom may be substituted on this atom by an acyl group, and in particular, by —C(=O)Me.

$C_{4-6}$ heterocyclyl methyl: —$CH_2$—($C_{4-6}$ heterocyclyl), wherein $C_{4-6}$ heterocyclyl is as defined above.

Phenyl: —$C_6H_5$, wherein the phenyl may itself be optionally substituted by one or more $C_{1-4}$ alkyl groups, one or more $C_{1-4}$ fluoroalkyl groups, one or more $C_{1-4}$ alkoxy groups, one or more halo substituents and one or more cyano substituents.

Benzyl: —$CH_2$-Phenyl, wherein phenyl is as defined above.

Halo: The term "halo" as used herein, refers to a group selected from fluoro, chloro, bromo and iodo.

Amido: —(C=O)NRR' wherein R and R' are independently selected from H, $C_{1-4}$ alkyl as defined above, or together form a group selected from (—$CH_2$—)$_n$ and —($CH_2$)$_m$—X—($CH_2$)$_p$—, where n=3-6, m and p=0-4, and X=O or NH. X may also be N—S(=O)$_2$, S or S(=O)$_2$. The cyclic amido groups may also be bridged by a further group selected from (—$CH_2$—)$_{n1}$ and —($CH_2$)$_{m1}$—X—($CH_2$)$_{p1}$—, where n1 is 1-3 and m1 and p1 are 1-3. The cyclic amido groups may also be further substituted by one, two or more hydroxy, oxo, $C_{1-2}$ alkyl and $C_{1-2}$ alkoxy groups or one spiro $C_{4-6}$ heteroaryl or spiro $C_{4-6}$ cycloalkyl group or be fused to an $C_{6-7}$ aromatic ring. Examples of amido groups include, but are not limited to, —C(=O)NH$_2$, —C(=O)NMe$_2$, —C(=O)NHMe, —C(=O)NHCH(CH$_3$)$_2$,

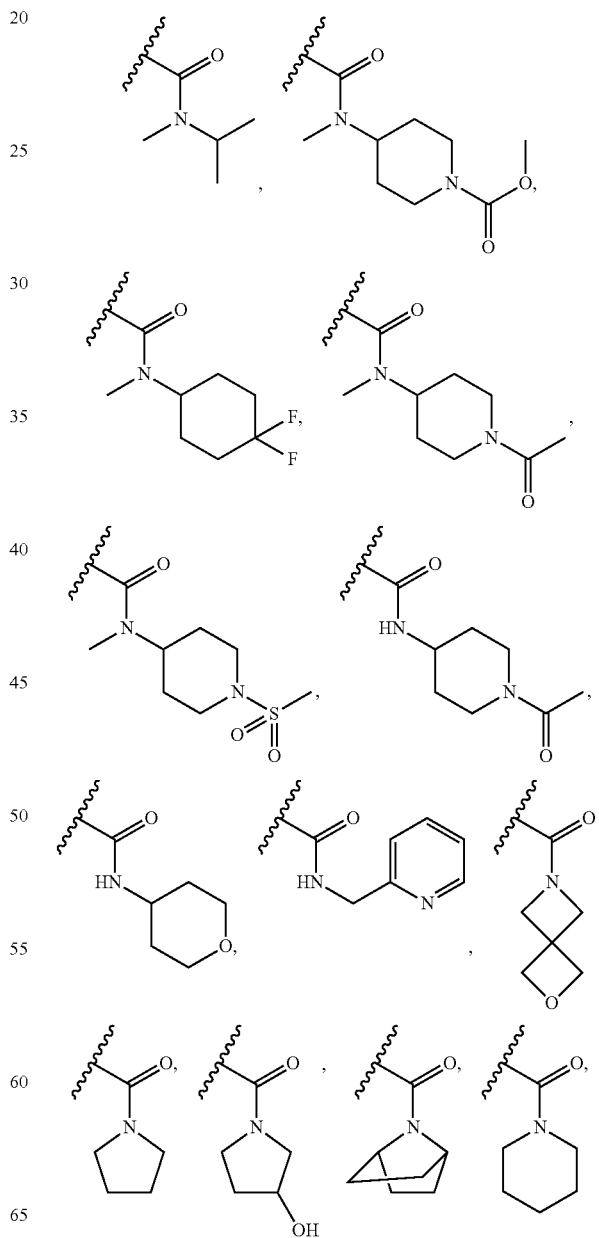

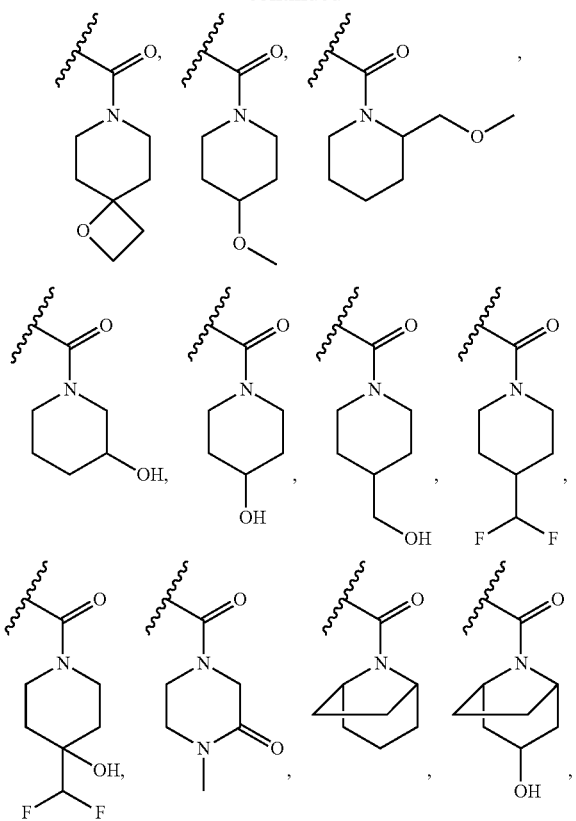
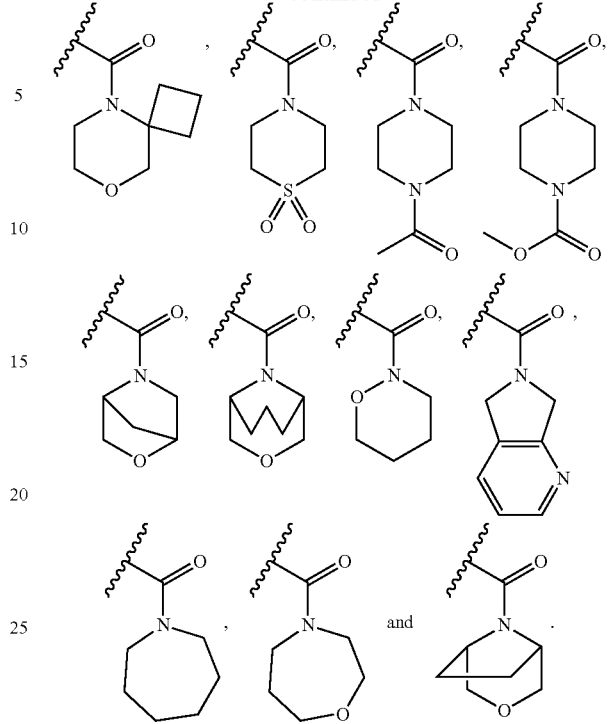

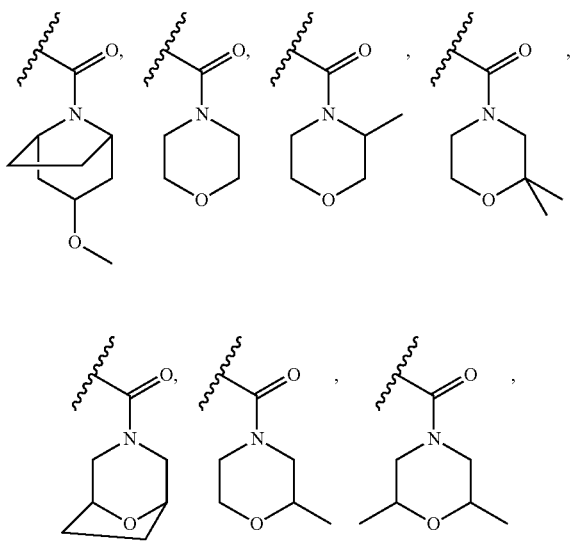

Amidomethyl: —CH$_2$-amido, where amido is as defined above, Examples of amidomethyl groups include, but are not limited to, —CH$_2$—C(=O)NH$_2$, —CH$_2$—C(=O)NMe$_2$, —CH$_2$—C(=O)NHMe,

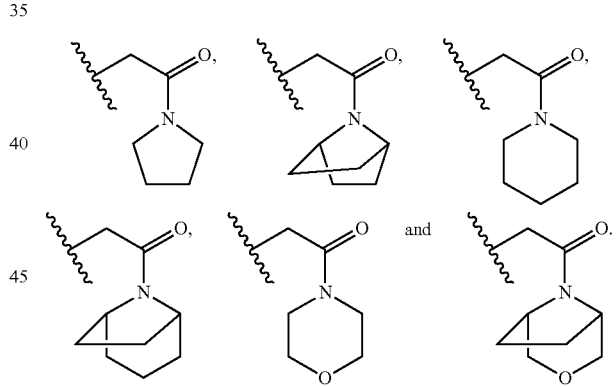

Acylamido: —NR(C=O)R' wherein R and R' are independently selected from H, C$_{1-4}$ alkyl and C$_{1-4}$ fluoro alkyl as defined above. R' may also be —(CH$_2$)$_n$—, where n is 3 or 4. Examples of an acylamido group include, but are not limited to, —N(H)C(=O)CF$_3$, —N(H)C(=O)Me, and:

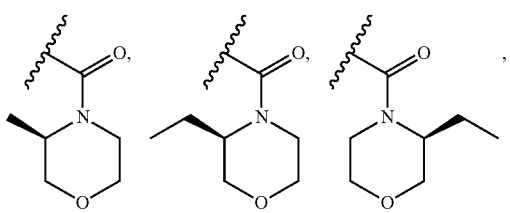
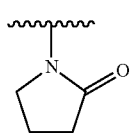 [SMILES: *N1CCCC1=O]

Acylamidomethyl: —CH$_2$-acylamido, where acylamido is as defined above, Examples of acylamidomethyl groups include, but are not limited to —CH$_2$—N(H)C(=O)Me and —CH$_2$—N(H)C(=O)CF$_3$.

$C_{1-4}$ alkyl ester: —C(=O)OR, wherein R is a $C_{1-4}$ alkyl group. Examples of $C_{1-4}$ alkyl ester groups include, but are not limited to, —C(=O)OCH$_3$, —C(=O)OCH$_2$CH$_3$, and —C(=O)OC(CH$_3$)$_3$.

$C_{1-4}$ alkyl ester methyl: —CH$_2$—($C_{1-4}$ alkyl ester), where $C_{1-4}$ alkyl ester is as defined above. Examples of $C_{1-4}$ alkyl ester methyl groups include, but are not limited to, —CH$_2$—C(=O)OCH$_3$, —CH$_2$—C(=O)OCH$_2$CH$_3$, and —CH$_2$—C(=O)OC(CH$_3$)$_3$.

$C_{1-4}$ alkyl carbamoyl: —NHC(=O)OR wherein R is a $C_{1-4}$ alkyl group as defined above. Examples of $C_{1-4}$ alkyl carbamoyl include, but are not limited to, —N(H)C(=O)OCH$_3$, —N(H)C(=O)OCH$_2$CH$_3$, and —N(H)C(=O)OC(CH$_3$)$_3$.

$C_{1-4}$ alkyl carbamoyl methyl: —CH$_2$—($C_{1-4}$ alkyl carbamoyl), where $C_{1-4}$ alkyl carbamoyl is as defined above. Examples of $C_{1-4}$ alkyl carbamoyl methyl include, but are not limited to, —CH$_2$—N(H)C(=O)OCH$_3$, —CH$_2$—N(H)C(=O)OCH$_2$CH$_3$, and —OH$_2$—N(H)C(=O)OC(CH$_3$)$_3$.

$C_{1-4}$ alkylacyl: —C(=O)R, wherein R is a $C_{1-4}$ alkyl group as defined above. Examples of $C_{1-4}$ alkylacyl groups include, but are not limited to, —C(=O)CH$_3$ (acetyl), —C(=O)CH$_2$CH$_3$ (propionyl) and —C(=O)C(CH$_3$)$_3$ (t-butyryl).

$C_{1-4}$ alkylacyl methyl: —CH$_2$—($C_{1-4}$alkylacyl), where $C_{1-4}$ alkylacyl is as defined above. Examples of $C_{1-4}$ alkylacylmethyl groups include, but are not limited to, —CH$_2$—C(=O)CH$_3$, —OH$_2$—C(=O)CH$_2$CH$_3$, and —CH$_2$—C(=O)C(CH$_3$)$_3$.

Phenylcarbonyl: —C(=O)-phenyl, where phenyl is as defined above.

Carboxy (carboxylic acid): —O(=O)OH

Carboxymethyl: —CH$_2$—C(=O)OH.

Ether: —OP, wherein P is chosen from one of the following substituents: $C_{1-4}$ alkyl, benzyl, phenyl, $C_{1-4}$ fluoroalkyl, $C_{5-6}$ heteroaryl, —CH$_2$—$C_{5-6}$ heteroaryl, $C_{4-6}$ heterocyclyl, and —CH$_2$—$C_{4-6}$ heterocyclyl as defined above. Examples of an ether include, but are not limited to, —OPh, —OBn, —OCF$_3$, —OCH(CH$_3$)$_2$, —OCH$_2$-cyclopropyl,

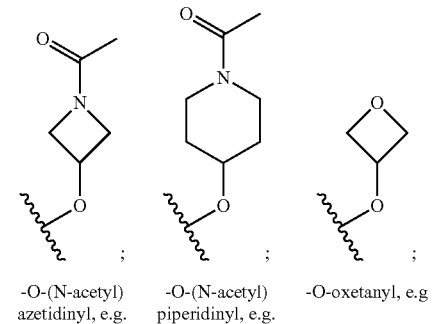

-O-(N-acetyl) azetidinyl, e.g.;    -O-(N-acetyl) piperidinyl, e.g.;    -O-oxetanyl, e.g

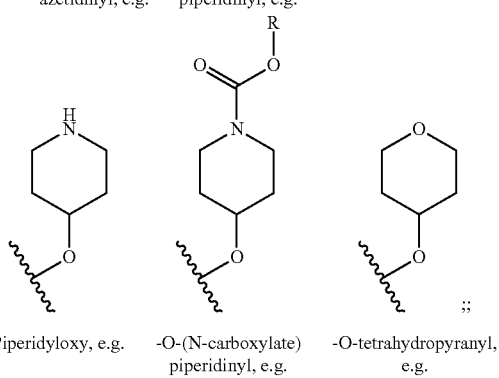

Piperidyloxy, e.g.    -O-(N-carboxylate) piperidinyl, e.g.    -O-tetrahydropyranyl, e.g.

where R is

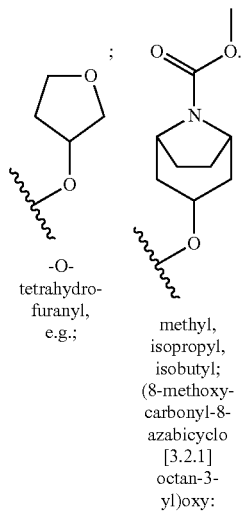

-O-tetrahydrofuranyl, e.g.;    methyl, isopropyl, isobutyl; (8-methoxy-carbonyl-8-azabicyclo[3.2.1]octan-3-yl)oxy:

Amino: —NPP', wherein P and P' are independently chosen from H, $C_{1-4}$ alkyl, $C_{4-6}$ heterocyclyl, phenyl and $C_{5-6}$ heteroaryl as defined above. Examples of an amine include, but are not limited to, —NH$_2$, —N(H)pyridazinyl,

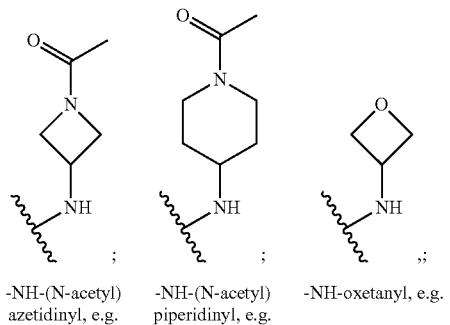

-NH-(N-acetyl) azetidinyl, e.g.    -NH-(N-acetyl) piperidinyl, e.g.    -NH-oxetanyl, e.g.

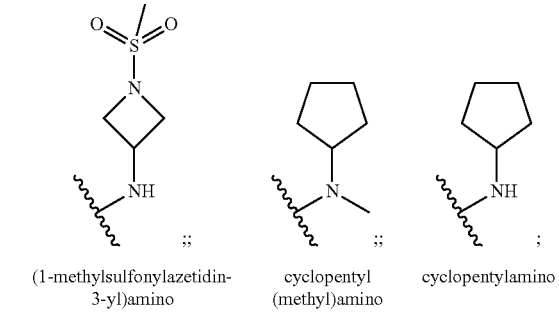

(1-methylsulfonylazetidin-3-yl)amino    cyclopentyl(methyl)amino    cyclopentylamino Aminomethyl: —CH$_2$-Amino, where amino is as defined above. Examples of aminomethyl include, but are not limited to, —CH$_2$—NH$_2$ and —CH$_2$—N(H)pyridazinyl.

Sulfonamido: —SO$_2$NRR' wherein R and R' are independently selected from H, $C_{1-4}$ alkyl, phenyl and $C_{5-6}$ heteroaryl as defined above. Examples of sulfonamido groups include, but are not limited to, —SO$_2$N(Me)$_2$ and —SO$_2$NPhMe.

Sulfonamino: —NHSO$_2$R wherein R is selected from $C_{1-4}$ alkyl, phenyl and $C_{5-6}$ heteroaryl as defined above. Examples of sulfonamino groups include, but are not limited to —NHSO$_2$Me and —NHSO$_2$Ph Sulfone: —SO$_2$R, wherein R is selected from C$_{1-4}$ alkyl and C$_{1-4}$ fluoroalkyl as defined above. Example of sulfone groups includes but is not limited to SO$_2$CF$_3$.

Sulfoxide: —SOR, wherein R is selected from C$_{1-4}$ alkyl and C$_{1-4}$ fluoroalkyl as defined above. Example of sulfoxide groups includes but is not limited to SOCF$_3$.

Nitrile: —CN.

Nitrilemethyl: —CH$_2$—CN

Fused N-heterocyclic ring: where A is phenyl, it may have a C$_{5-6}$ N$_1$-containing heterocyclic ring fused to it as a substituent group. The C$_{5-6}$ N$_1$-containing heterocyclic ring may in particular be selected from:

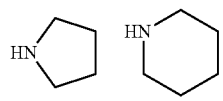

Which may be fused in any orientation, and wherein the N ring atom may be optionally substituted, for example by a C$_{1-4}$ alkylacyl group.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N+HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_{2+}$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric.

Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

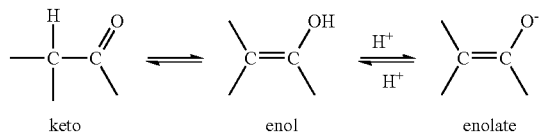

keto          enol          enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), 11C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of cancers and hemaglobinopathies.

Cancer

Modulators of PRMT5 mediated post-translational arginine methylation of p53 may regulate a pro-apoptotic p53 response, and may therefore be useful as therapeutic agents, for example in the treatment of cancer. Such agents may also be useful as therapeutic agents for the treatment of cancers which exhibit overexpression of PRMT5.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor. Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chondrosarcoma, osteosarcoma).

The cancer may be a PRMT5 overexpressing cancer. The cancer may over express PRMT5 protein relative to non-cancerous tissue. In some cases, the cancer overproduces PRMT5 mRNA relative to non-cancerous tissue.

Alternatively or additionally, the cancer may be a p53 overexpressing cancer. The cell may overexpress p53 protein relative to non-cancerous tissue. It may overproduce p53 mRNA as compared to non-cancerous tissue. In some cases, the level of p53 protein and/or mRNA in the cell is at a level approximately equivalent to that of a non-cancerous cell.

The agents described herein may be useful in combination with other anti-cancer therapies. They may act synergistically with chemo- or radiotherapy, and/or with p53 targeted drugs.

An inhibitor of PRMT5 would in all likelihood augment the effects of drugs (such as the nutlins) that restore p53. Inhibition of PRMT5, resulting in decreased arginine-methylated p53, may sensitize tumour cells to chemo- and radiotherapy by switching, or at least biasing, the cellular outcome to apoptosis.

Combination Therapies p53 is activated by DNA damage. PRMT5 is part of the complex of proteins that activate and modulate p53 activity in response to DNA damage. It is likely that inhibition of PRMT5, resulting in decreased arginine-methylated p53, would sensitize tumour cells to chemo- and radiotherapy by switching or at least biasing the cellular outcome to apoptosis. PRMT5 inhibition is likely to synergize well with low dose chemo- or radiotherapy, by stabilizing p53, and biasing the cellular outcome to apoptosis.

Biasing the p53 response towards apoptosis would in all likelihood be of benefit, and an agent that so biases the response would be expected to augment the effect of a p53 resurrecting drug. Thus, in some cases, a PRMT5 modulator disclosed herein may be administered in conjunction with a radiotherapeutic or chemotherapeutic regime. It may be administered in conjunction with a drug that resurrects cellular p53 activity, for example, a p53 agonist. The PRMT5 modulator may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

Hemoqlobinopathies

The compounds disclosed herein may be useful in the treatment or prevention of conditions that may benefit from the increased expression of γ-globin genes, for example, due to the release of repressive methylation of these genes. The compounds disclosed herein may be useful in the treatment or prevention of hemoglobinopathies. A hemoglobinopathy is a condition associated with the presence of abnormal hemoglobin in the blood of a subject. Such conditions include β-thalassemia and Sickle Cell Disease, α-thalassemia and δ-thalassemia.

Hemoglobinopathies treatable by the compounds disclosed herein may be ameliorated by the re-activation of the subjects γ-globin genes (γ genes). In such cases, the subject is not a fetal mammal.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5'-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825;

J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors, aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 ρg/mL, for example from about 10 ng/ml to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example, one skilled in the art may use a diverse range of synthetic methods to synthesise the desired compounds such as but not limited to methods described in literature (for example, but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula I (and Ia), as described above, can be prepared by synthetic strategies outlined below, wherein the definitions above apply.

General Synthesis Method 1

Scheme 1A illustrates the formation of the amide bond by coupling a relevant carboxylic acid to a primary amine or a secondary amine (G1). Methods to form such amides will be apparent to those skilled in the art, but include for example, the use of reagents such as HATU, HBTU, T3P and EDCl/HOBt, and the use of activated forms of the carboxylic acid such as the corresponding acyl halide, mixed anhydride or N-hydroxysuccinimide ester.

Scheme 1A

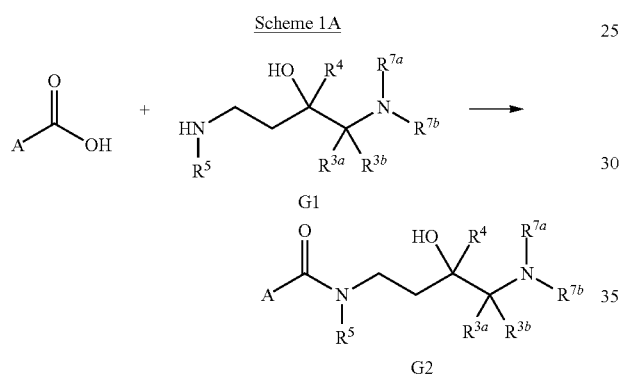

where $R^{7a}$ and $R^{7b}$ and the N atom to which they are bound represent the fused ring system.

Where A contains a direct carboxylic acid substitution or a further substitution that also has a carboxylic acid substitution (G3), another amide formation can be conducted to provide compounds of G4, scheme 1B. Coupling is possible with a primary or secondary amine or cyclised secondary amine including, but not limited to, azetidine, pyrrolidine, piperidine, piperazine and morpholine.

Scheme 1B

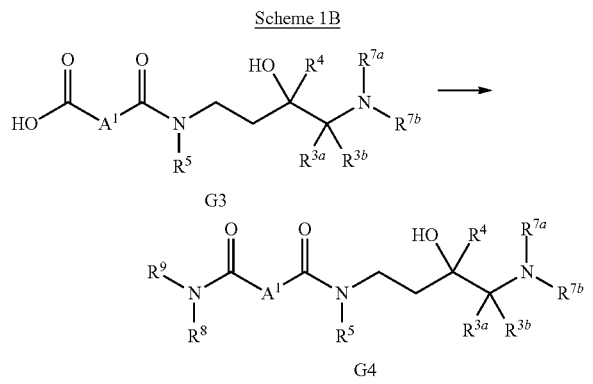

General Synthesis Method 2

Scheme 2A illustrates the synthesis of the substituted amine alcohol (G7) in a stereochemically pure form. This is achieved by opening the epoxide with a desired amine (HNR$^{7a}$R$^{7b}$) to form the intermediate G6. The phthalimide protecting group can then be removed by heating with hydrazine hydrate to form G7, other suitable protecting groups and removal methods will be known to those skilled in the art (for example, *Greene's Protective Groups in Organic Synthesis*, 4th Edition).

Scheme 2A

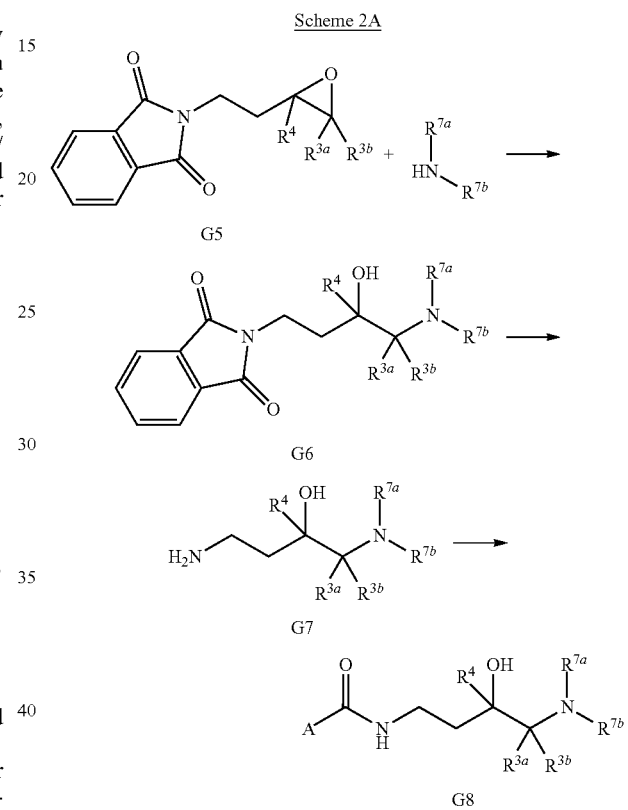

The amide formation to form G8 can be achieved by the methods outlined in Scheme 1A. The synthesis of epoxide G5 will be apparent to those skilled in the art but include coupling of phthalimide or its metal salts with an alkyl halide or sulfonate bearing an epoxide as shown in Scheme 2B. The group denoted by (X) can be but is not limited to halogen, tosylate or nosylate. The group denoted by (M) can be but is not limited to hydrogen, alkali metal salts such as Li, Na, K.

Scheme 2B

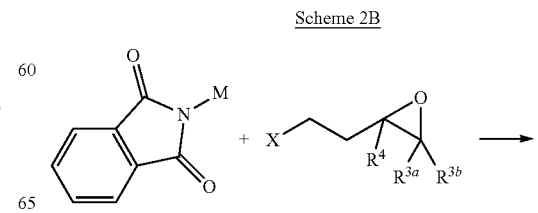

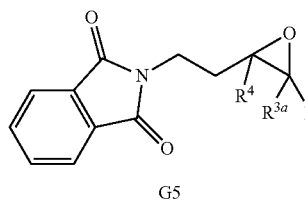

G5

General Synthesis Method 3

Scheme 3A illustrates an approach to the synthesis of compounds with the formula of G13, beginning with the reaction of the desired amine ($HNR^{7a}R^{7b}$) with an epoxide G10 bearing a suitable protected amino group. Opening of the epoxide under suitable conditions furnishes the intermediate compound G11. Suitably protected amino groups and methods for the removal of said protecting groups will be known to those skilled in the art (for example, *Greene's Protective Groups in Organic Synthesis*, 4th Edition). Upon removal of the protecting group to provide compounds of the general formula G12, these intermediates can be converted to the desired compound, G13, by the procedure outlined in Scheme 1A.

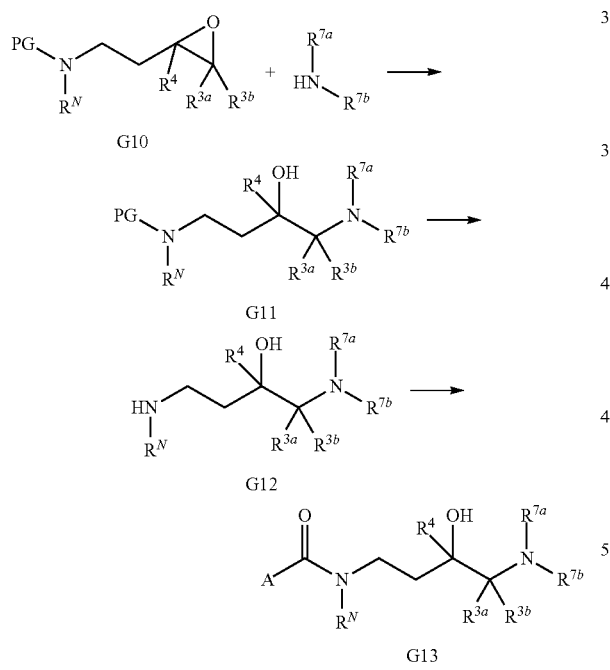

Alternatively, enantiomerically pure forms of the epoxide G10 can be used to obtain the products G13 in enantiomerically pure form.

General Synthesis Method 4

Scheme 4A illustrates how to form amine substitutions such as shown in G14. An amide is reacted with a halo-epoxide or similar and the resultant mixture reacted on with a desired amine ($HNR^{7a}R^{7b}$) resulting in a product within the scope of G14. The group denoted (X) can be but is not limited to halogen, tosylate, nosylate or similar.

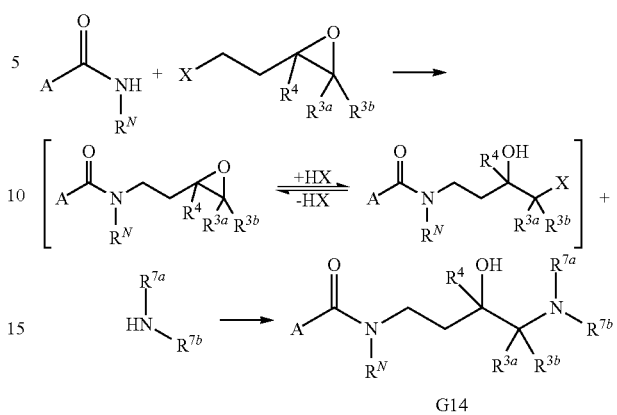

Alternatively, enantiomerically pure forms of the halo-epoxide can be used to obtain the products G14 in enantiomerically pure form.

General Synthesis Method 5

Scheme 5A illustrates how to form amine substitutions such as shown in G16. Suitable amide protecting groups and methods for the removal of said protecting groups will be known to those skilled in the art (for example, *Greene's Protective Groups in Organic Synthesis*, 4th Edition). The group denoted (X) can be but not limited to halogen, tosylate, nosylate or similar. An amide is reacted with a halo epoxide and the resultant mixture reacted on with a desired amine ($HNR^{7a}R^{7b}$) resulting in an intermediate (G15). Removal of the protecting group provides compounds of the general formula G16.

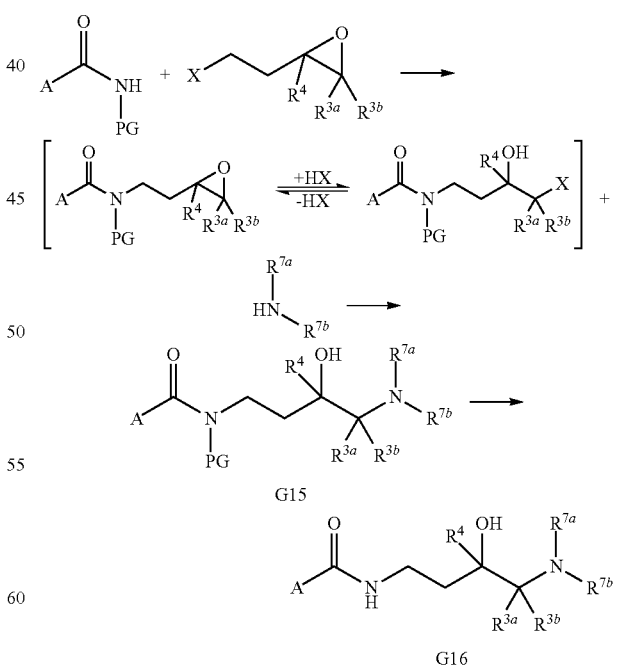

Alternatively, enantiomerically pure forms of the halo-epoxide can be used to obtain the products G16 in enantiomerically pure form.

General Synthesis Method 6

Scheme 6A illustrates the synthesis of compounds G20 which begins with a coupling of a compound G17 with a desired amine (HNR$^{7a}$R$^{7b}$) by an S$_N$2 displacement of a leaving (LG) to give intermediates G18. The group represented by (LG) includes but is not limited to halide, mesylate, tosylate, nosylate. The group represented by (PG) is a suitable amine protecting group which includes but is not limited to Boc, phthalimide, benzyl, PMB, allyl. Suitable amine protecting groups and methods for the removal of said protecting groups will be known to those skilled in the art (for example, *Greene's Protective Groups in Organic Synthesis,* 4th Edition). Upon removal of the protecting group to form G19, coupling with a suitable carboxylic acid can be performed by methods illustrated in Scheme 1A.

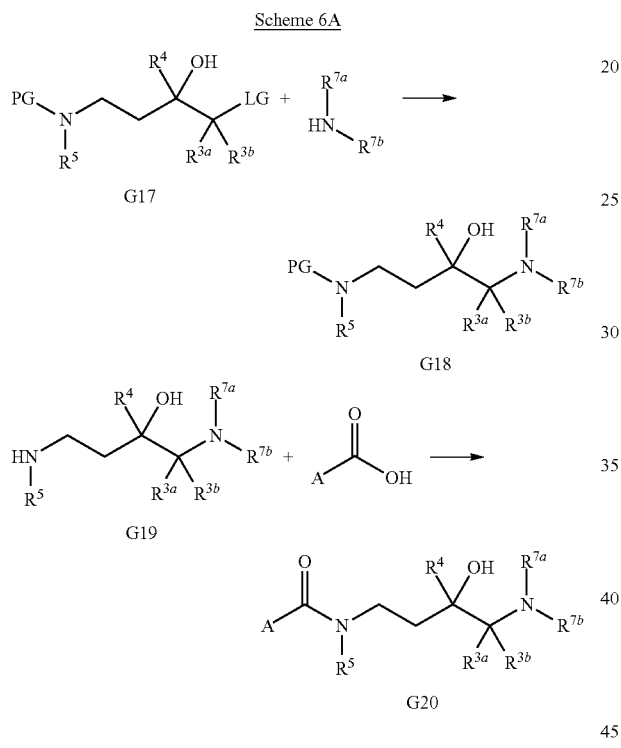

Alternatively, as shown in Scheme 6B, compounds with structure G21 can be coupled with the desired amine (HNR$^{7a}$R$^{7b}$) to give compounds G20.

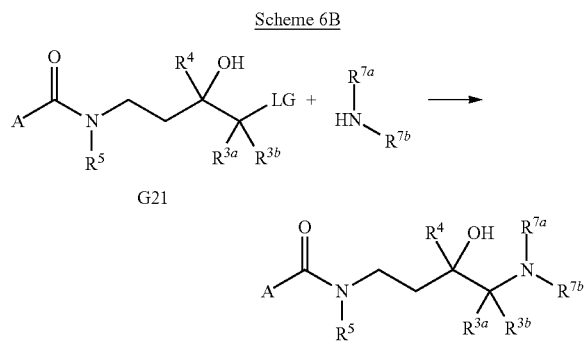

General Synthesis Method 7

Scheme 7A illustrates the addition of an amine (HNR$^8$R$^9$), as a substituent which is a part of A. This can be achieved by coupling a relevant carboxylic acid to a primary amine or a secondary amine, NHR$^8$R$^9$. Methods to form such amides will be apparent to those skilled in the art, including for example, the use of reagents such as HATU, HBTU, T3P and EDCl/HOBt, and the use of activated forms of the carboxylic acid such as the corresponding acyl halide, mixed anhydride or N-hydroxysuccinimide ester. The group denoted by (X) may be, but is not limited to; a halogen, tosylate or other suitable leaving group. Conversion of (X) in G22 into an ester in G23 will be apparent to those skilled in the art, including for example, a carbonylation reaction which may be achieved using carbon monoxide in the presence of a transition metal catalyst such as but not limited to; PdCl$_2$dppf.DCM; and an alcoholic solvent such as but not limited to; methanol, ethanol, isopropanol or tert-butyl alcohol. Formation of the carboxylic acid can be achieved by, for example, hydrolysis with a base such as an alkali metal hydroxide or an acid for example, aqueous hydrochloric acid to form G24. The amide formation to form G25 can be achieved by the methods outlined in Scheme 1A.

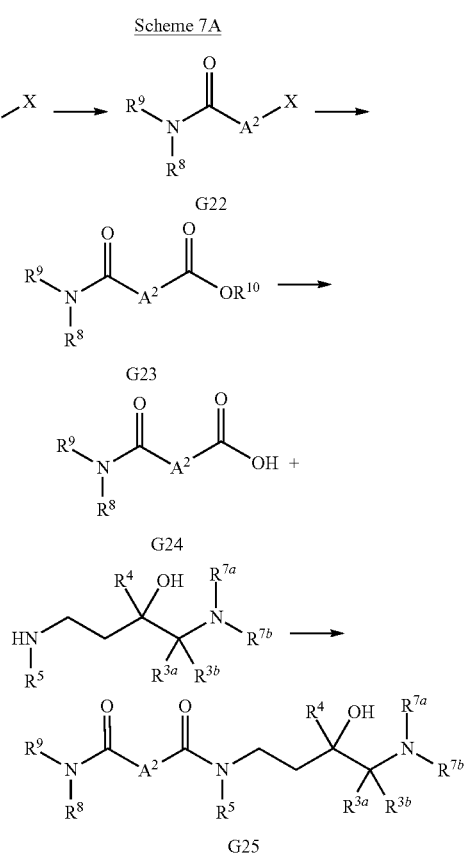

Alternatively, for the synthesis of ester G23 the order of steps may be reversed as described in Scheme 7B.

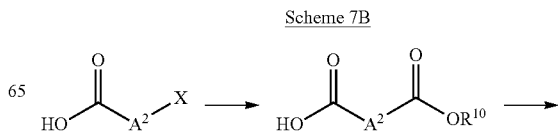

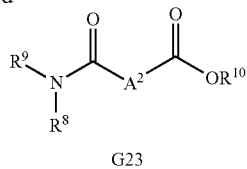

G23

General Synthesis Method 8

Scheme 8A illustrates the addition of an $R^{11}$ group, as a substituent which is part of A. This can be achieved using any suitable coupling reaction known to a person skilled in the art—for example, by Suzuki coupling. The groups denoted by $R^{11}X$ and $B^1$ are chosen to be suitable for the coupling reaction employed. For example, in the case of a Suzuki coupling reaction (X) may be a halogen, tosylate or other suitable group and $B^1$ represents a suitable boron compound including, but not limited to, a boronic acid or boronic ester.

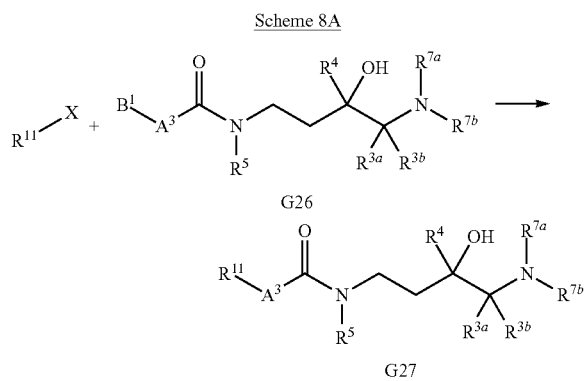

Examples of $B^1$ that can be used in the Suzuki coupling include, but are not limited to, those shown below.

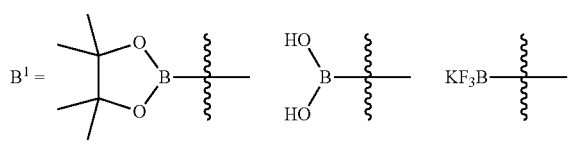

The types of $R^{11}X$ compounds that can be used in the Suzuki coupling include, but are not limited to, those shown in Table 1.

TABLE 1

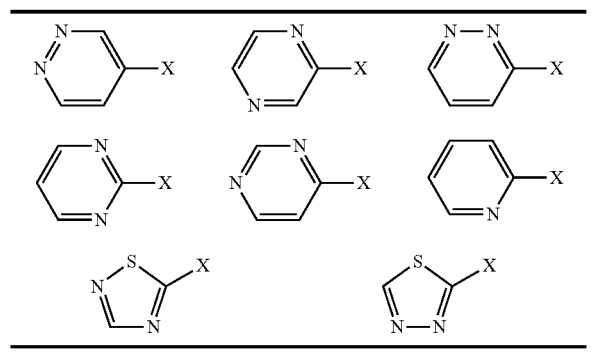

In addition to scheme 8A, the position of the (X) and ($B^1$) can be reversed as shown below in scheme 8B, to give the same final compound G27. Similarly to Scheme 8A, the groups denoted by $R^{11}B^1$ and (X) are chosen to be suitable for the coupling reaction employed. For example, in the case of a Suzuki coupling reaction (X) may be a halogen, tosylate or other suitable group and $R^{11}B^1$ represents a suitable boron compound including, but not limited to, a boronic acid of boronic ester.

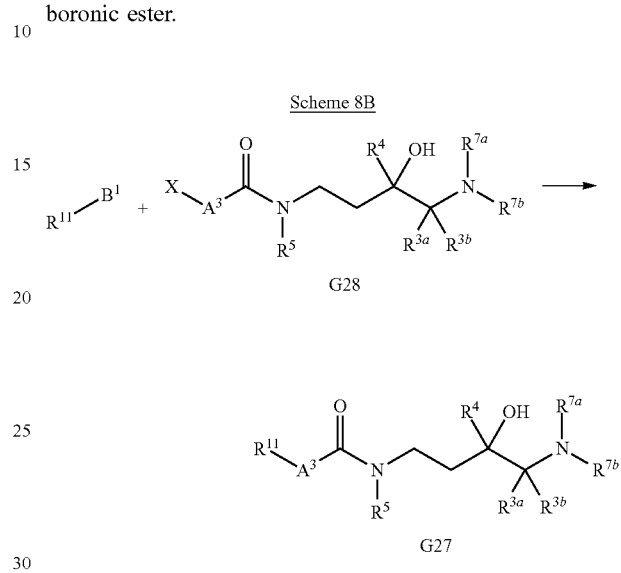

The types of $R^{11}B^1$ compounds that can be used in the Suzuki coupling include, but are not limited to, those shown in Table 2.

TABLE 2

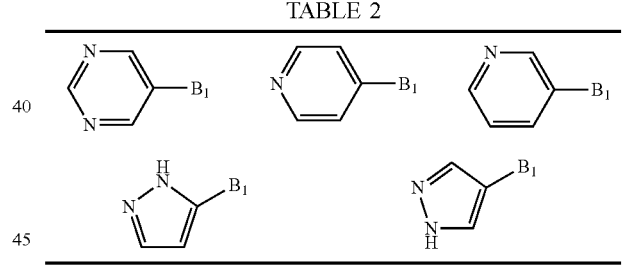

A variety of coupling reactions may be used to introduce the $R^{11}$ group other than Suzuki coupling, such as for example, transition metal catalysed coupling reactions of for example, tin (Stille type reaction) and zinc (Negishi type reaction) compounds. Substitution of the halogen by suitable nucleophiles in the presence or absence of other reagents such as for example, transition metal compounds is also suitable.

Coupling reactions may also be used to prepare the carboxylic acids used in Scheme 1A for the amide formations, as shown in scheme 8C. In starting material G30 and G32, A as described herein, consists of -$A^3X$ and -$A^3B^1$ respectively. In the product G33, A as described herein, consists of -$A^3R^{11}$. The groups denoted by (X) and $B^1$ are chosen to be suitable for the coupling reaction employed. For example, in the case of a Suzuki coupling reaction (X) may be a halogen, tosylate or other suitable group and $B^1$ represents a suitable boron compound including, but not limited to, a boronic acid of boronic ester.

Scheme 8C

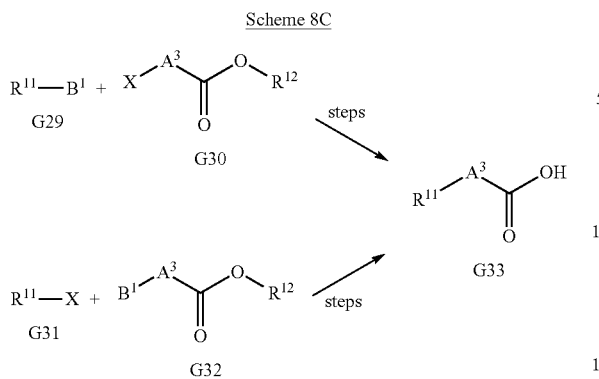

Scheme 9B

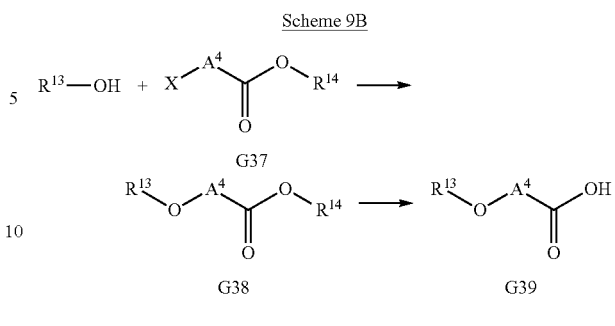

In G30 and G32 $R^{12}$ can be a H or a carbon group for example, but not limited to Me, Et, Pr, iPr, Bu, t-Bu. It may be necessary to form the carboxylic acid before use in the amide coupling (Scheme 1A), generally this may be achieved by for example, hydrolysis with a base such as an alkali metal hydroxide or an acid for example, aqueous hydrochloric acid to form G33. The same method for converting an ester to a carboxylic acid is used in other general schemes.

General Synthesis Method 9

Scheme 9A illustrates the addition of an $R^{13}$ group, as a substituent which is part of A. This can be achieved using any suitable coupling reaction known to the person skilled in the art, for example, by an SnAr displacement or Buchwald coupling. The group denoted by (X) may be but not limited to halogen and is chosen to be suitable for the coupling reaction employed.

Scheme 9A

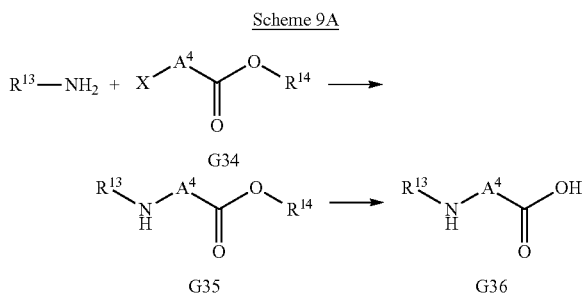

In G34 and G35 $R^{14}$ can be a H or a carbon group for example but not limited to Me, Et, Pr, iPr, Bu, t-Bu. In these instances in may be necessary to form the carboxylic acid before use in an amide coupling (Scheme 1A), generally this can be achieved by, for example, hydrolysis with a base such as an alkali metal hydroxide or an acid, for example, aqueous hydrochloric acid to form G36. The same method for converting an ester to a carboxylic acid is used in other general schemes.

Alternatively, to synthesise ether linked compounds, a similar strategy can be employed as shown in Scheme 9B. This can be achieved using any suitable coupling reaction known to a person skilled in the art, for example, by an SnAr displacement or an Ullman-type coupling to give compounds with structure G38. Upon hydrolysis using methods previously described, compounds with structure G39 may be obtained and used in an amide bond formation as shown in scheme 1A.

FURTHER EMBODIMENTS $R^1$

In some embodiments, there may be no $R^1$ substituents. In some embodiments, $R^1$ represents one to four Me or halo groups, preferably one to three Me or halo groups and more preferably one or two Me or halo groups. In some of these embodiments, $R^1$ may represent F. In others of these embodiments, $R^1$ may represent Me groups.

$R^2$ $R^{2a}$, $R^{2b}$, $R^{2c}$ and $R^{2d}$ are independently selected from H, F, $CH_2OH$ and Me. In some of these embodiments, $R^{2a}$, $R^{2b}$, $R^{2c}$ and $R^{2d}$ are independently selected from H, Me and $CH_2OH$. In further of these embodiments, $R^{2a}$, $R^{2b}$, $R^{2c}$ and $R^{2d}$ are independently selected from H and Me.

In some embodiments $R^{2a}$, $R^{2b}$, $R^{2c}$ and $R^{2d}$ are all H.

In some embodiments $R^{2a}$, $R^{2b}$, $R^{2c}$ and $R^{2d}$ are comprised of three H and one Me or $CH_2OH$ group. It may be preferred in these embodiments that $R^{2a\ is}$ Me and $R^{2b}$, $R^{2c}$ and $R^{2d}$ are H. It may be preferred in these embodiments that $R^{2c}$ is Me or $CH_2OH$ and $R^{2a}$, $R^{2b}$ and $R^{2d}$ are H.

In some embodiments $R^{2a}$, $R^{2b}$, $R^{2c}$ and $R^{2d}$ are comprised of two H and two Me groups. It may be preferred in these embodiments that $R^{2a}$ and $R^{2c}$ are Me and $R^{2b}$ and $R^{2d}$ are H. It may be preferred in these embodiments that $R^{2a}$ and $R^{2b}$ are Me and $R^{2c}$ and $R^{2d}$ are H. It may also be preferred in these embodiments that $R^{2c}$ and $R^{2d}$ are Me and $R^{2a}$ and $R^{2b}$ are H.

$R^3$ $R^{3a}$ and $R^{3b}$ are independently selected from H and Me. In some embodiments $R^{3a}$ is H and $R^{3b}$ is Me. In some embodiments $R^{3a}$ and $R^{3b}$ are both H. In some embodiments $R^{3a}$ and $R^{3b}$ are both Me.

$R^4$

In some embodiments $R^4$ is H. In some embodiments $R^4$ is Me.

$R^5$

In some embodiments $R^5$ is H. In some embodiments $R^5$ is Me.

Enantiomers

The carbon to which $R^4$ is attached is a chiral centre.

When the compound contains this chiral centre, in some embodiments, the compound is a racemate.

When the compound contains this chiral centre, in some embodiments, the compound is a single enantiomer. In some of these embodiments, the compound is the (R)-enantiomer. In others of these embodiments, the compound is the (S)-enantiomer.

$R^1$-$R^5$

In some embodiments, $R^1$, $R^{2a}$, $R^{2b}$, $R^{2c}$, $R^{2d}$, $R^{3a}$, $R^{3b}$, $R^4$ and $R^5$ are all H, and thus the compound of formula I is of formula Ia:

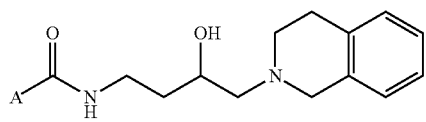
(Ia)

A

Optional Substituents

When the optional substituent on A is $C_{1-4}$ alkyl, it may be preferably selected from methyl, ethyl, i-Pr, t-Bu.

When the optional substituent on A is $C_{1-4}$ fluoroalkyl, it may preferably be selected from —$CF_3$ and —$CF_2H$.

When the optional substituent on A is $C_{5-6}$ heteroaryl, it may be substituted by one or more $C_{1-4}$ alkyl groups. These groups may preferably be on one or more of the nitrogen ring atoms (if present). These groups may also preferably be methyl.

When the optional substituent on A is $C_{5-6}$ heteroaryl, it may preferably be selected from pyridizinyl, pyrimidinyl, pyridinyl, pyrazolyl, pyrazinyl, oxadiazolyl, isoxazolyl, triazolyl, imidazolyl, benzimidazolyl and thiadiazolyl.

When the optional substituent on A is $C_{5-6}$ heteroaryl methyl, it may preferably be selected from —$CH_2$-imidazolyl and —$CH_2$-triazolyl.

When the optional substituent on A is $C_{5-6}$ heterocyclyl, it may preferably be morpholino.

When the optional substituent on A is $C_{5-6}$ heterocyclyl methyl, it may preferably be selected from —$CH_2$-morpholino and —$CH_2$-piperazinyl.

When the optional substituent on A is phenyl, it may be substituted by one or more $C_{1-4}$ alkyl groups. These groups may preferably be methyl.

When the optional substituent on A is phenyl, it may be substituted by one or more $C_{1-4}$ fluoroalkyl groups. These groups may preferably be trifluoromethyl.

When the optional substituent on A is phenyl, it may be substituted by one or more $C_{1-4}$ alkoxy groups. These groups may preferably be methoxy.

When the optional substituent on A is phenyl, it may be substituted by one or more halo substituents. These groups may preferably be fluoro or chloro, more preferably fluoro.

When the optional substituent on A is phenyl, it may be substituted by one or more cyano groups. It may be preferred that there is a single cyano substituent.

When the optional substituent on A is halo, it may preferably be selected from F, Cl and Br.

When the optional substituent on A is amido, the amido substituent groups R and R' may preferably form a ring, which ring may also be bridged or substituted. If the amido group is not cyclic, it may preferably be selected from —C(=O)$NH_2$, —C(=O)NMeH, —C(=O)$NMe_2$ and —C(=O)$N^iPrH$. If the amido group is cyclic, it may preferably be selected from —C(=O)-piperidinyl, —C(=O)-hydroxypiperidinyl, —C(=O)-methoxypiperidinyl, —C(=O)-pyrrolidinyl, —C(=O)-morpholino, —C(=O)-methylmorpholino, —C(=O)-dimethylmorpholino and —C(=O)-azetidinyl. Further cyclic amido groups include:

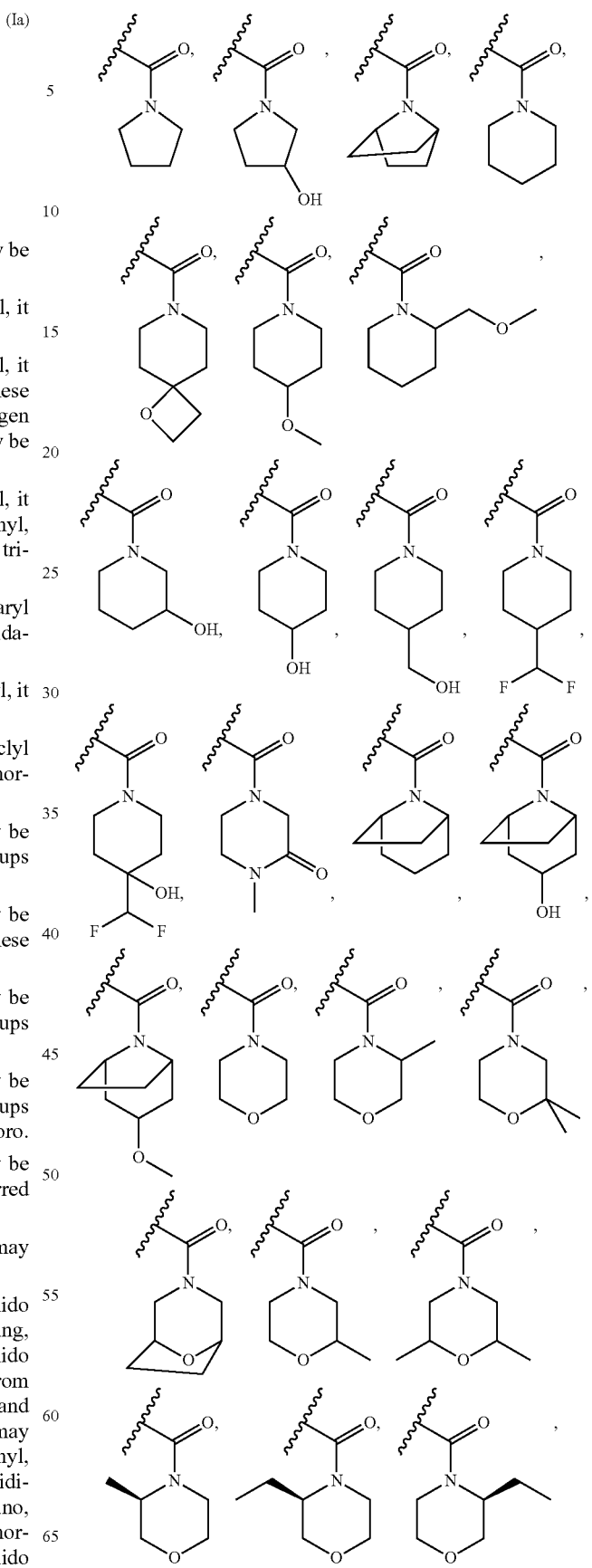

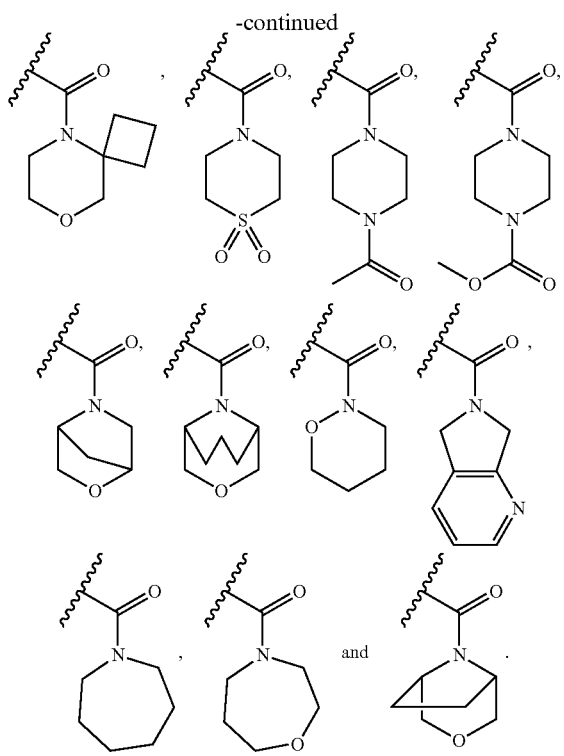

When the optional substituent on A is amidomethyl, the amido substituent groups R and R' may preferably form a ring, which ring may also be bridged or substituted. If the amido group is not cyclic, the amidomethyl group may preferably be selected from —CH$_2$C(=O)NH$_2$, —CH$_2$C(=O)NMeH and —CH$_2$C(=O)N$^i$PrH. If the amido group is cyclic, the amidomethyl group may preferably be selected from —CH$_2$C(=O)-pyrrolidinyl —CH$_2$C(=O)-morpholino, —C(=O)-hydroxypiperidinyl, —C(=O)-methoxypiperidinyl, —C(=O)-methylmorpholino and CH$_2$C(=O)-azetidinyl. Further cyclic amidomethyl groups include:

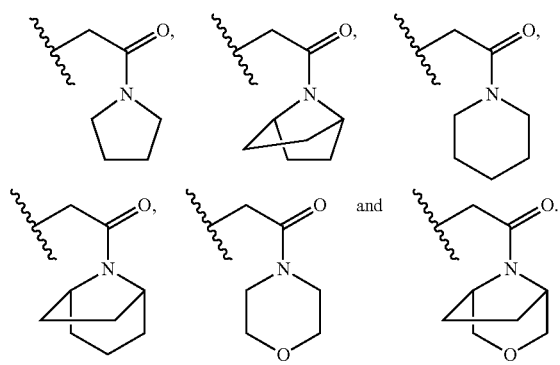

When the optional substituent on A is acylamido, it may preferably be γ-lactam.

When the optional substituent on A is acylamidomethyl, it may preferably be selected from —CH$_2$NHC(=O)Me, —CH$_2$NHC(=O)CF$_3$.

When the optional substituent on A is C$_{1-4}$ alkyl ester, it may preferably be —C(=O)—OMe.

When the optional substituent on A is C$_{1-4}$ alkyl ester methyl, it may preferably be —CH$_2$—C(=O)—OMe.

When the optional substituent on A is C$_{1-4}$ alkyl carbamoyl methyl, it may preferably be —CH$_2$NHC(=O)OMe.

When the optional substituent on A is C$_{1-4}$ alkylacyl, it may preferably be selected from —C(=O)Me and —C(=O)Et.

When the optional substituent on A is C$_{1-4}$ alkylacylmethyl, it may preferably be —CH$_2$C(=O)Me.

When the optional substituent on A is phenylcarbonyl, it may preferably be —C(=O)-Ph.

When the optional substituent on A is ether, it may preferably be selected from methoxy, ethoxy, —OBn, —OPh, —OCF$_3$, —OCF$_2$H, —O—(C$_6$H$_4$)—CN, —O-oxanyl, —OCH$_2$pyridinyl, —OCH$_2$-oxadiazolyl, —OCH$_2$-isoxazole.

When the optional substituent on A is amino, the amino substituent may be a C$_{5-6}$ heteroaryl group, in which case the amino group may preferably be selected from —NH-pyrazinyl, —NH-pyrimidine. In other embodiments, the amino substituent may be a C$_{4-6}$ heterocyclyl group, such as optionally N-substituted azetidinyl, optionally N-substituted piperidinyl and oxetanyl. A further amino group may be:

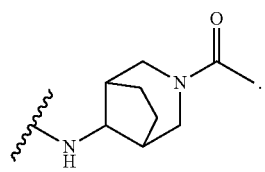 [SMILES: *NC1C2CCC1CN(C(C)=O)C2]

When the optional substituent on A is aminomethyl, it may preferably be —CH$_2$NH$_2$. Alternatively, the amino substituent may be as defined above.

When the optional substituent on A is sulfonamido it may preferably be selected from —SO$_2$NMePh, —SO$_2$NMe$_2$, and —SO$_2$NHEt.

When the optional substituent on A is sulfonamino, it may preferably be selected from —NHSO$_2$Ph and —NHSO$_2$Me.

When the optional substituent on A is sulfone, it may preferably be —SO$_2$CF$_3$.

Optionally Substituted Phenyl

In some embodiments A may be an optionally substituted phenyl.

In some of these embodiments, A is unsubstituted phenyl.

In some of these embodiments, the phenyl of A has 1, 2, 3, 4 or 5 substituents.

In some of these embodiments, the phenyl of A has 1 or 2 substituents.

It may be preferred that in some of these embodiments R$^1$, R$^{2a}$, R$^{2b}$, R$^{2c}$, R$^{2d}$, R$^{3a}$, R$^{3b}$, R$^4$ and R$^5$ are all hydrogen.

It may be preferred in some of these embodiments that at least one of R$^1$, R$^{2a}$, R$^{2b}$, R$^{2c}$, R$^{2d}$, R$^{3a}$, R$^{3b}$, R$^{4b}$ and R$^5$ is not hydrogen.

It may be preferred in some of these some of these embodiments that R$^{1-5}$ are such that the compound is of formula Ia.

It may be preferred in these embodiments that the optional substituents are independently selected from the following: C$_{1-4}$ alkyl; C$_{1-4}$ fluoroalkyl; C$_{3-6}$ cycloalkyl; C$_{5-6}$ heteroaryl; C$_{5-6}$ heteroaryl methyl; C$_{4-6}$ heterocyclyl; C$_{4-6}$ heterocyclyl methyl; phenyl; benzyl; halo; amido; amidomethyl; acylamido; acylamidomethyl; C$_{1-4}$ alkyl ester; C$_{1-4}$ alkyl ester methyl; C$_{1-4}$ alkyl carbamoyl; C$_{1-4}$alkyl carbamoyl methyl; C$_{1-4}$ alkylacyl; C$_1$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: C$_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—CN, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted by one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetraydropyanyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$CF$_3$— γ-lactam, —CH$_2$NHC(=O)Me, —CH$_2$NHC(=O)OMe, —CH$_2$NHC(=O)CF$_3$, morpholino, —CH$_2$NH$_2$, —C(=O)Ph, —OCH$_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

In may be preferred in these embodiments that, when the optional substituent is a C$_{5-6}$ heteroaryl group, the heteroaryl ring itself is substituted with one or more C$_{1-4}$ alkyl groups.

In may be preferred in the above embodiments that 1 substituent is present. In may be preferred in the above embodiments that 2 substituents are present.

Halo and methoxy substituents may be preferred in the ortho position of the phenyl group. Amido and amidomethyl substituents may be preferred in the para position of the phenyl group.

In some embodiments, the phenyl group bears a halo or methoxy substituent in the ortho position, and an amido or amidomethyl substituent in the para position of the phenyl group.

In some embodiments, the phenyl group bears an amino substituent in the meta position.

Where the substituent on phenyl is a fused C$_{5-6}$ N$_1$-containing heterocyclic ring, A may have a core structure selected from:

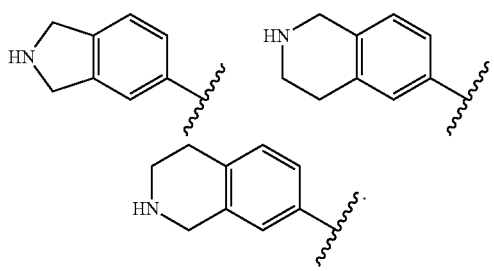

Particular A groups of interest include:

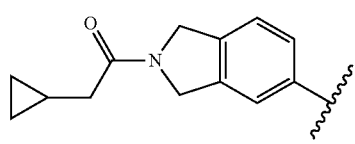

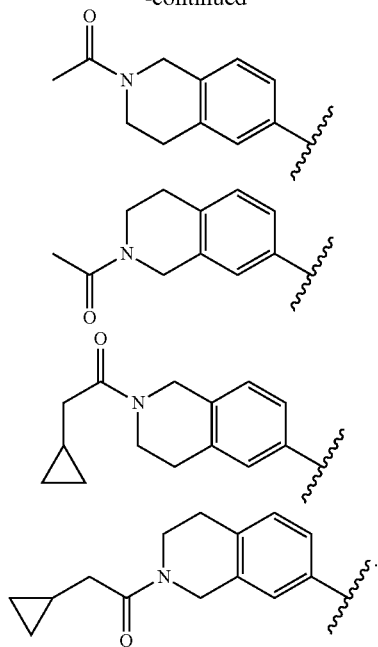

Optionally Substituted Naphthyl

When A is naphthyl, it may be in any orientation, e.g. naphth-1-yl, naphth-2-yl.

In some embodiments A may be optionally substituted naphthyl.

In some of these embodiments, A is unsubstituted naphthyl.

In some of these embodiments, the naphthyl ring of A has 1, 2, 3, 4 or 5 substituents.

In some of these embodiments, the naphthyl ring of A has 1 or 2 substituents.

It may be preferred that in some of these embodiments R$^1$, R$^{2a}$, R$^{2b}$, R$^{2c}$, R$^{2d}$, R$^{3a}$, R$^{3b}$, R$^4$ and R$^5$ are all hydrogen.

It may be preferred in some of these embodiments that at least one of R$^1$, R$^{2a}$, R$^{2b}$, R$^{2c}$, R$^{2d}$, R$^{3a}$, R$^{3b}$, R$^4$ and R$^5$ is not hydrogen.

It may be preferred in some of these some of these embodiments that R$^{1-5}$ are such that the compound is of formula Ia.

It may be preferred in these embodiments that the optional substituents refers to 0-2 substituents independently selected from the following: C$_{1-4}$ alkyl; C$_{1-4}$ fluoroalkyl; C$_{3-6}$ cycloalkyl; C$_{5-6}$ heteroaryl; C$_{5-6}$ heteroaryl methyl; C$_{4-6}$ heterocyclyl; C$_{4-6}$ heterocyclyl methyl; phenyl; benzyl; halo; amido; amidomethyl; acylamido; acylamidomethyl; C$_{1-4}$ alkyl ester; C$_{1-4}$ alkyl ester methyl; C$_{1-4}$ alkyl carbamoyl; C$_{1-4}$ alkyl carbamoyl methyl; C$_{1-4}$ alkylacyl; C$_{1-4}$ alkyl acyl methyl; phenylcarbonyl; carboxy; carboxymethyl; ether; amino; aminomethyl; sulfonamido; sulfonamino; sulfone; nitrile; and nitrilemethyl.

It may be preferred in these embodiments that 1 substituent is present. In may be preferred in these embodiments that 2 substituents are present.

Optionally Substituted C$_{5-12}$ Heteroaryl

In some embodiments A may be an optionally substituted C$_{5-12}$ heteroaryl group.

In some of these embodiments, A is unsubstituted C$_{5-12}$ heteroaryl group.

In some of these embodiments, the C$_{5-12}$ heteroaryl of A has 1, 2, 3, 4 or 5 substituents.

In some of these embodiments, the $C_{5-12}$ heteroaryl of A has 1 or 2 substituents.

It may be preferred in these embodiments that the $C_{5-12}$ heteroaryl ring is selected from one of the following: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl. The heteroatoms may be in any location in the ring, which may be joined to the remainder of the molecule via a ring carbon atom. It may be further preferred that the $C_{5-12}$ heteroaryl ring is either pyridinyl or pyrimidinyl. It may also be further preferred that the $C_{5-12}$ heteroaryl is selected from pyridyl, pyrimidinyl, oxazolyl, oxadiazolyl, pyrazolyl and thiazolyl and in particular:

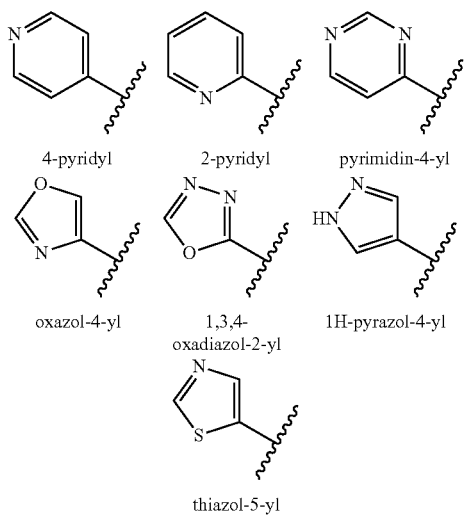

Further preferred groups may include benzothiazolyl and benzimidazolyl and in particular:

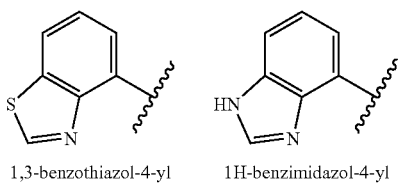 [SMILES: *c1cccc2scnc12 ; *c1cccc2[nH]cnc12]

It may be preferred that in some of these embodiments $R^1$, $R^{2a}$, $R^{2b}$, $R^{2c}$, $R^{2d}$, $R^{3a}$, $R^{3b}$, $R^4$ and $R^5$ are all hydrogen.

It may be preferred in some of these embodiments that at least one of $R^1$, $R^{2a}$, $R^{2b}$, $R^{2c}$, $R^{2d}$, $R^{3a}$, $R^{3b}$, $R^4$ and $R^5$ is not hydrogen.

It may be preferred in some of these some of these embodiments that $R^{1-5}$ are such that the compound is of formula Ia.

It may be preferred in these embodiments that the optional substituents are independently selected from the following: $C_{1-4}$ alkyl; $C_{1-4}$ fluoroalkyl; $C_{3-6}$ cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phenylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: $C_{1-4}$ alkyl; $C_{1-4}$ fluoroalkyl; $C_{5-6}$ heteroaryl, $C_{4-6}$ heterocyclyl; phenyl; halo; and ether.

It may be preferred in these embodiments that the optional substituent are selected from; methyl, ethyl, butyl, chloro, bromo, fluoro, morpholino, pyrrolidinyl, —OBn, —OPh, phenyl, para-bromophenyl, pyrazolyl, pyrimidinyl, imidazolyl and —$CF_3$.

In may be preferred in these embodiments that 1 substituent is present. In may be preferred in these embodiments that 2 substituents are present.

Halo and methoxy substituents may be preferred in the ortho position of a $C_6$ heteroayl group, or α-position of $C_5$ and $C_{7-12}$ heteroaryl group. Amido and amidomethyl substituents may be preferred in the para position of a $C_6$ heteroayl group, or γ-position of $C_5$ and $C_{7-12}$ heteroaryl group.

In some embodiments, a $C_6$ heteroayl group bears a halo or methoxy substituent in the ortho position, and an amido or amidomethyl substituent in the para position.

In some embodiments, a $C_6$ heteroayl group bears an amino substituent in the meta position. In some embodiment, a $C_5$ or $C_{7-12}$ heteroaryl group bears an amino substituent in the β-position.

In some embodiments A is selected from one of the following groups:

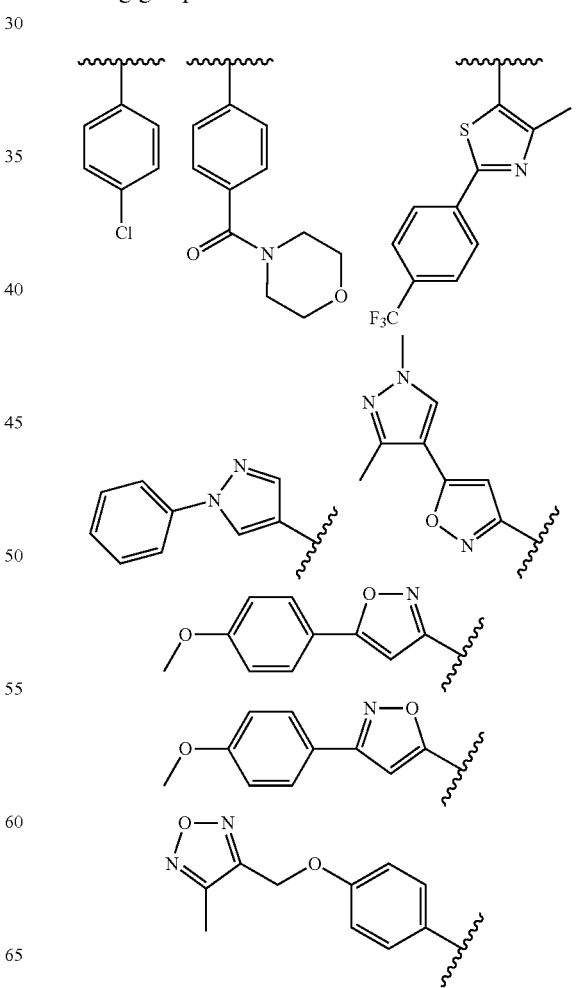

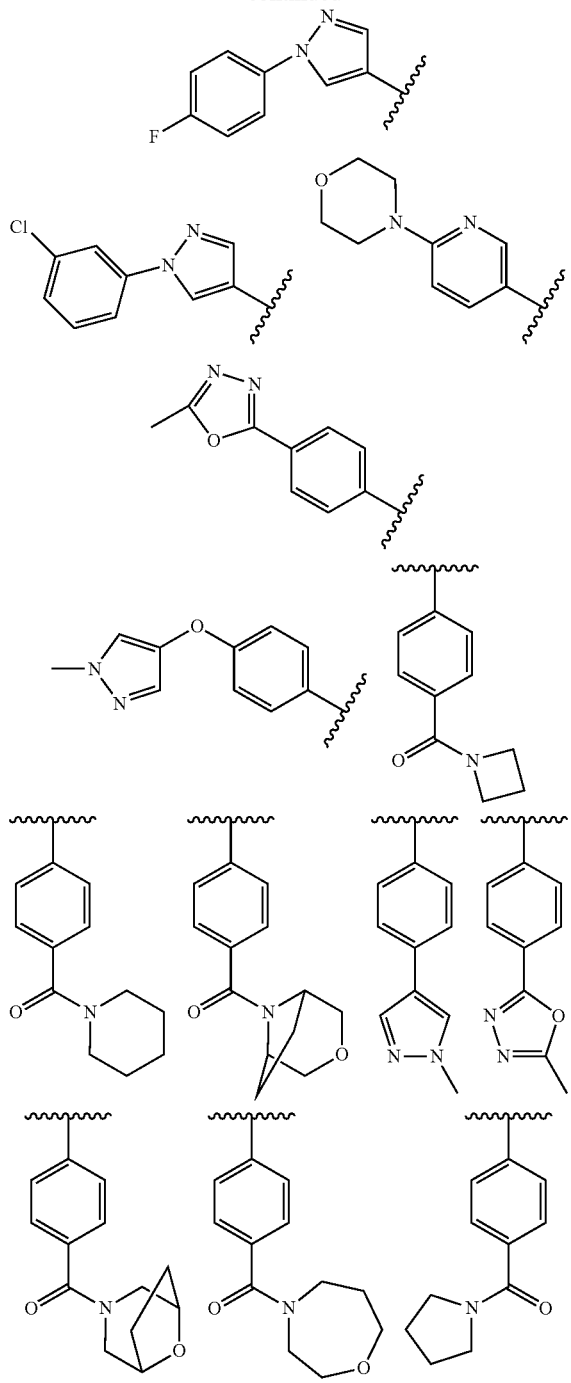
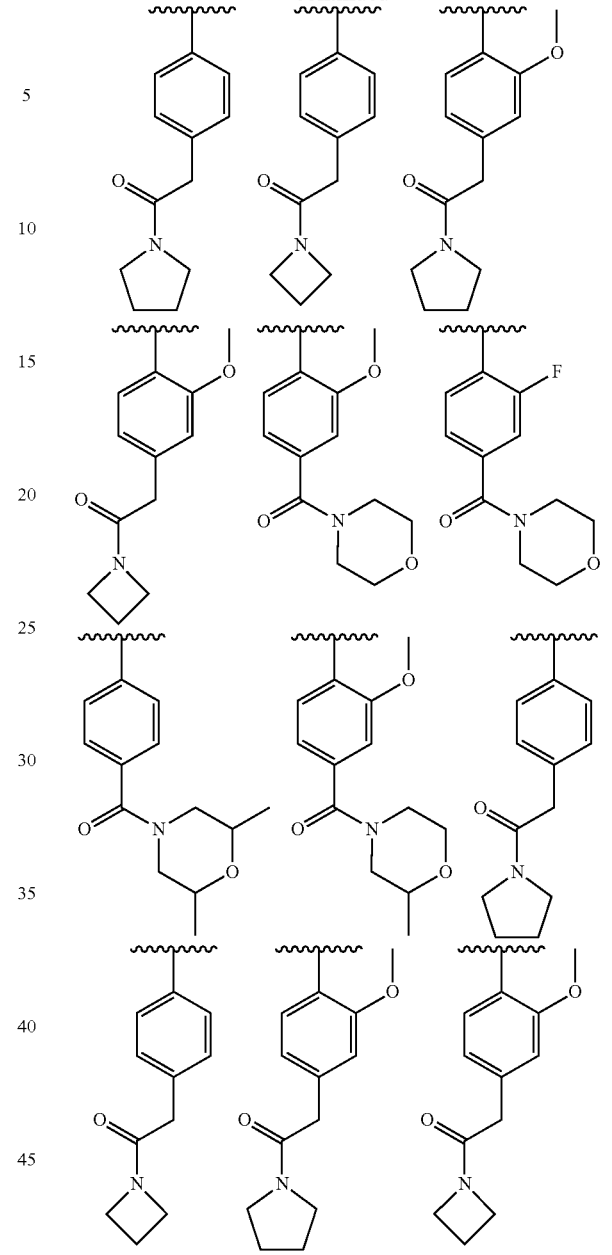
In some embodiments A may be selected from one of the following groups:
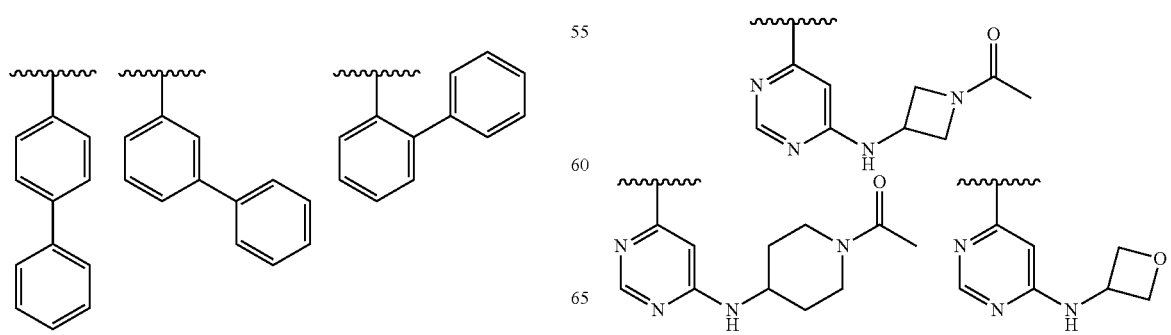

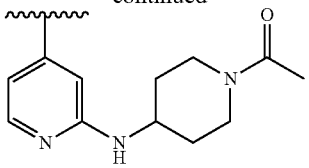

It may be preferred that in some of these embodiments $R^1$, $R^{2a}$, $R^{2b}$, $R^{2c}$, $R^{2d}$, $R^{3a}$, $R^{3b}$, $R^4$ and $R^5$ are all hydrogen.

In some embodiments, A may be selected from:

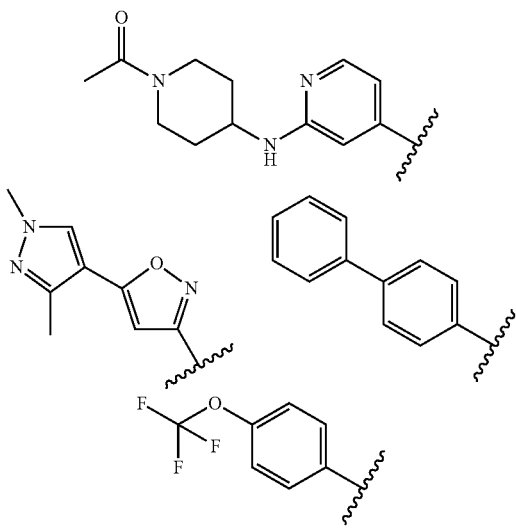

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), trimethylsilyl (TMS), and acetyl (Ac).

For convenience, many chemical compounds are represented using well known abbreviations, including but not limited to, methanol (MeOH), deuterated methanol ($d_4$-MeOD) ethanol (EtOH), isopropanol (i-PrOH), ether or diethyl ether ($Et_2O$), ethyl acetate (EtOAc), acetic acid (AcOH), acetonitrile (MeCN), dichloromethane (methylene chloride, DCM), trifluoroacetic acid (TFA), N,N-dimethylformamide (DMF), tetrahydrofuran (THF), dimethylsulfoxide (DMSO), deuterated chloroform ($CDCl_3$), diethylamine (DEA), deuterated dimethylsulfoxide ($d_6$-DMSO), N-ethyl-N'-(3-dimethylaminopropyl)carbodiimide hydrochloride (EDCl.HCl, EDCl), meta-chloroperoxybenzoic acid (mCPBA), 1,1'-bis(diphenylphosphino)ferrocene (dppf), 2-dicyclohexylphosphino-2',6'-diisopropoxybiphenyl (Ruphos), tert-butyloxycarbonyl (Boc, BOC), 2-(trimethylsilypethoxymethyl) (SEM), triethylamine ($Et_3N$), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA), lithium bis (trimethylsilyl)amide (LiHMDS) magnesium sulfate ($MgSO_4$), 1,1'-bis(diphenylphosphino)ferrocene dichloropalladium (II) ($PdCl_2$(dppf)), trans-dichlorobis(triphenylphosphine)palladium(II) ($PdCl_2(PPh_3)_2$), tris(dibenzylideneacetone) dipalladium(0) ($Pd_2(dba)_3$), Propylphosphonic anhydride (T3P), tetra-n-butylammonium bromide (TBAB), and 1-hydroxybenzotriazole (HOBt).

General Experimental Details

Unless otherwise stated the following generalisations apply. $^1$H NMR spectra were recorded on a Bruker Ultrashield plus (400 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

LC/MS data was generated using either an Agilent 6100 Series Single Quad LC/MS (LCMS-A) or Agilent 1260 Infinity Series UPLC/MS (LCMS-B). Chlorine isotopes are reported as $^{35}$Cl, Bromine isotopes are reported as either $^{79}$Br or $^{81}$Br or both $^{79}$Br/$^{81}$Br.

Preparative mass-directed LC was carried out using a Waters ZQ 3100.

LCMS Method A (LCMS-A)
  Instrument: Agilent 6100 Series Single Quad LC/MS
  Agilent 1200 Series HPLC
  Pump: 1200 Series G1311A Quaternary pump
  Autosampler: 1200 Series G1329A Thermostatted Autosampler
  Detector: 1200 Series G1314B Variable Wavelength Detector
  LC conditions:
  Reverse Phase HPLC analysis
  Column: Luna C8 (2) 5 μm 50×4.6 mm 100 Å
  Column temperature: 30° C.
  Injection Volume: 5 μL
  Solvent A: Water 0.1% Formic Acid
  Solvent B: MeCN 0.1% Formic Acid
  Gradient: 5-100% B over 10 min
  Detection: 254 nm or 214 nm
  MS conditions:
  Ion Source: Quadrupole
  Ion Mode: Multimode-ES
  Drying gas temp: 300° C.
  Vaporizer temperature: 200° C.
  Capillary voltage (V): 2000 (positive)
  Capillary voltage (V): 4000 (negative)
  Scan Range: 100-1000
  Step size: 0.1 sec
  Acquisition time: 10 min
LCMS Method B (LCMS-B:)
  Instrument:
  Pump: 1260 Infinity G1312B Binary pump
  Autosampler: 1260 Infinity G1367E 1260 HiP ALS
  Detector: 1290 Infinity G4212A 1290 DAD
  LC conditions:
  Reverse Phase HPLC analysis
  Column: Poroshell 120 EC-C18 2.7 μm 50×3.0 mm
  Column temperature: 35° C.
  Injection Volume: 1 μL
  Solvent A: Water 0.1% Formic Acid
  Solvent B: MeCN 0.1% Formic Acid
  Gradient: 5-100% B over 3.8 min
  Detection: monitored at 254 nm and 214 nm MS conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
Additional Cartridges used are as follows Phase Separator
Manufacturer: Biotage
Product: ISOLUTE® Phase Separator (3 mL unless otherwise stated)
SCX and SCX-2 Cartridges
Manufacturer: Biotage
Product: ISOLUTE® SCX-2 1 g (6 mL Column)
Manufacturer: Silicycle
Product: SCX-2 500 mg or 5 g
Manufacturer: Agilent
Product: Bond Elut® SCX 10 g
Sample Extraction Cartridge
Manufacturer: Waters
Product: Oasis® HLB 35 cc (6 g) LP extraction cartridge Example 1: 4-Chloro-N-(4-(3,4-dihydroisoquinolin-2(1H)-yl)-3-hydroxybutyl)benzamide (1)

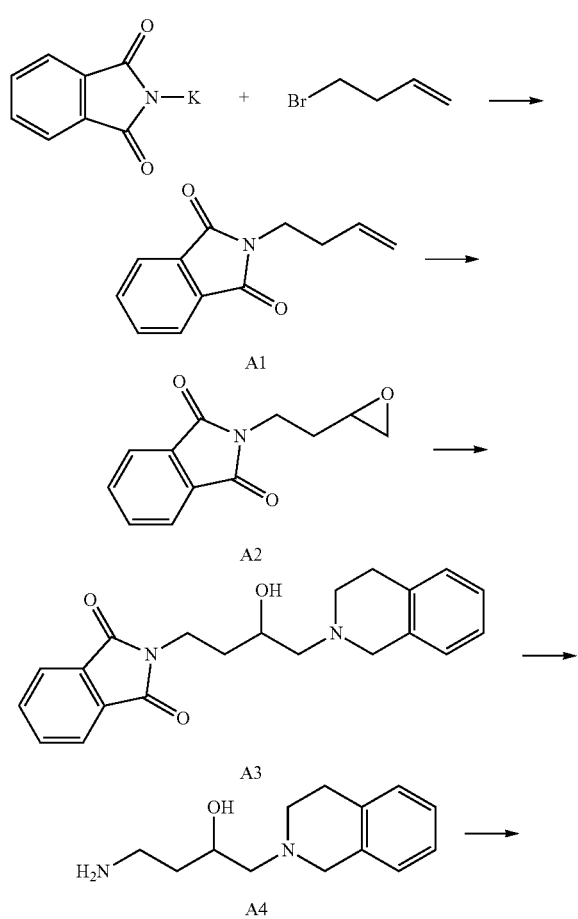

-continued

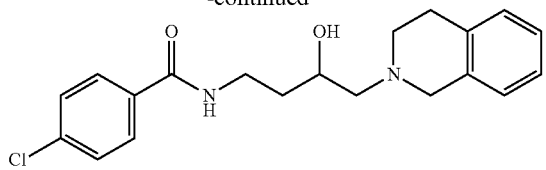

1

(a) 2-(But-3-en-1-yl)isoindoline-1,3-dione (A1)

Potassium phthalimide (500 mg, 2.70 mmol), acetonitrile (5 mL) and 4-bromobut-1-ene (0.548 mL, 5.40 mmol) were stirred at 90° C. After 18 hours, the mixture was cooled to room temperature, filtered and the collected solids were washed with ethyl acetate (5 mL). The combined filtrates were concentrated and column chromatography (12 g $SiO_2$ cartridge, 0-100% ethyl acetate in petroleum benzine 40-60° C.) gave the desired compound as a white solid (431 mg, 79%). $^1$H NMR (400 MHz, $CDCl_3$) δ 7.87-7.80 (m, 2H), 7.73-7.67 (m, 2H), 5.86-5.72 (m, 1H), 5.11-4.99 (m, 2H), 3.77 (t, J=7.1 Hz, 2H), 2.49-2.40 (m, 2H). LCMS-B RT 3.71 min; m/z 202.1 $[M+H]^+$.

(b) 2-(2-(Oxiran-2-yl)ethyl)isoindoline-1,3-dione (A2)

2-(But-3-en-1-yl)isoindoline-1,3-dione A1 (428 mg, 2.13 mmol), chloroform (5 mL) and 70-75% m-CPBA (629 mg, 2.55 mmol) were stirred at room temperature. After 18 hours, the mixture was quenched with a 10% w/v aqueous solution of sodium thiosulfate (2.5 mL) and was stirred vigorously for 5 minutes. The mixture was diluted with a saturated aqueous solution of sodium bicarbonate (5 mL), water (20 mL) and chloroform (10 mL). The separated aqueous phase was extracted with chloroform (2×10 mL). The combined organic extracts were dried over sodium sulfate and concentrated in vacuo to give the desired compound as a white solid (451 mg, 98%). The material was carried forward without further purification. $^1$H NMR (400 MHz, $CDCl_3$) δ 7.88-7.82 (m, 2H), 7.74-7.69 (m, 2H), 3.97-3.80 (m, 2H), 3.03-2.94 (m, 1H), 2.74-2.68 (m, 1H), 2.47-2.41 (m, 1H), 2.04-1.93 (m, 1H), 1.90-1.79 (m, 1H); LCMS-B RT 3.43 min; m/z 218.1 $[M+H]^+$ (c) 2-(4-(3,4-Dihydroisoquinolin-2(1H)-yl)-3-hydroxybutyl)isoindoline-1,3-dione (A3)

2-(2-(Oxiran-2-yl)ethyl)isoindoline-1,3-dione A2 (100 mg, 0.46 mmol), dry acetonitrile (2 mL), tetrahydroisoquinoline (0.061 mL, 0.48 mmol) and calcium triflate (78 mg, 50 mol %) were stirred at room temperature. After two hours, the mixture was purified by column chromatography (12 g $SiO_2$ cartridge, 0-10% methanol/DCM) to give the desired compound as a pale yellow syrup (44 mg, 27%): $^1$H NMR (400 MHz, $d_4$-methanol) δ 7.88-7.76 (m, 4H), 7.11-6.96 (m, 4H), 3.97-3.76 (m, 3H), 3.75-3.62 (m, 2H), 2.93-2.75 (m, 4H), 2.59-2.55 (m, 2H), 1.96-1.86 (m, 1H), 1.84-1.68 (m, 1H); LCMS-B m/z: 351.2 $[M+H]^+$.

(d) 4-Amino-1-(3,4-dihydroisoquinolin-2(1H)-yl)butan-2-ol (A4)

2-(4-(3,4-Dihydroisoquinolin-2(1H)-yl)-3-hydroxybutyl)isoindoline-1,3-dione A3 (44 mg, 0.13 mmol), ethanol (2 mL) and hydrazine hydrate (0.2 mL) were stirred at 80° C. for 3 hours. The mixture was cooled to room temperature, the resulting slurry was filtered and the collected solids were washed with cold ethanol (2 mL). The combined filtrates were concentrated to give the desired compound as a white semi-solid (29 mg, >100%). The material was carried forward without further purification (e) 4-Chloro-N-(4-(3,4-dihydroisoquinolin-2(1H)-yl)-3-hydroxybutyl)benzamide (1)

4-Amino-1-(3,4-dihydroisoquinolin-2(1H)-yl)butan-2-ol A4 (28 mg, 0.13 mmol), MeCN (2 mL), DIPEA (0.044 mL, 0.25 mmol) and 4-chlorobenzoyl chloride (0.016 mL, 0.13 mmol) were stirred at room temperature. After 18 hours, methanol (0.1 mL) was added and the mixture loaded onto a 5 g SCX cartridge. The cartridge was washed with methanol (40 mL) then eluted with 3.5 M ammonia in methanol (40 mL). The basic eluate was concentrated in vacuo and the material was purified by preparative TLC (SiO$_2$, 5% methanol/DCM) to give the desired compound as a white solid (21 mg, 46%): $^1$H NMR (400 MHz, d$_4$-methanol) δ 7.80-7.76 (m, 2H), 7.46-7.42 (m, 2H), 7.14-6.98 (m, 4H), 4.02-3.93 (m, 1H), 3.78-3.65 (m, 2H), 3.61-3.46 (m, 2H), 2.95-2.80 (m, 4H), 2.65-2.53 (m, 2H), 1.92-1.81 (m, 1H), 1.76-1.65 (m, 1H); LCMS-A RT 1.55 min; m/z 359.1 [M+H]$^+$.

Intermediate Preparation (i) Alternate Synthesis of 4-amino-1-(3,4-dihydroisoquinolin-2(1H)-yl)butan-2-ol (A4)

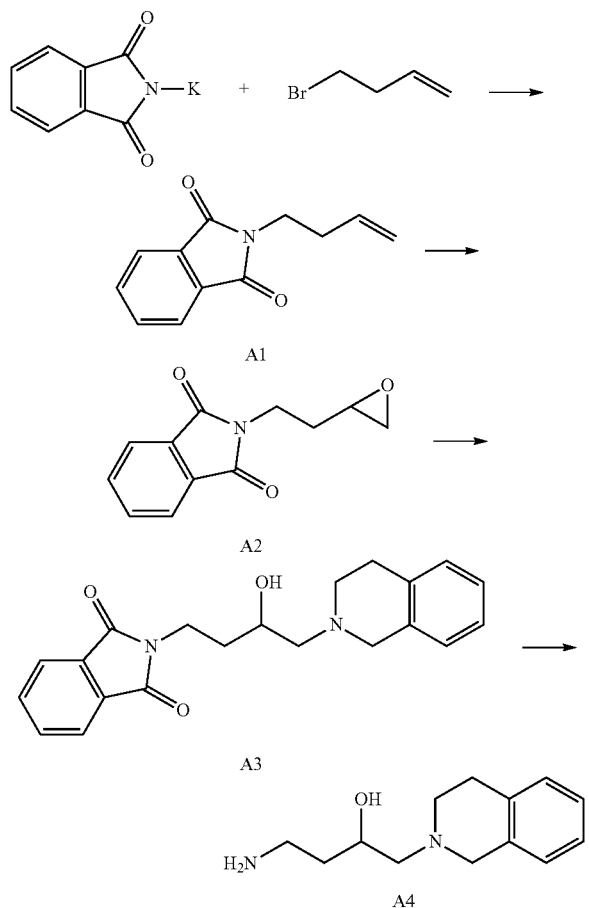

(a) 2-(but-3-en-1-yl)isoindoline-1,3-dione (A1)

Potassium phthalamide (5.00 g, 27.0 mmol), acetonitrile (50 mL) and 4-bromobut-1-ene (5.48 mL, 54.0 mmol) were stirred at 90° C. After 18 hours the mixture was cooled to room temperature, filtered and the collected solids washed with ethyl acetate (5 mL). The combined filtrates were evaporated, chromatography (40 g silica cartridge, 10-60% ethyl acetate/petroleum benzine) gave the title compound as a white solid (4.31 g, 79% yield). LCMS-B: rt 3.71 min; m/z (positive ion) 202.1 [M+H]$^+$ (b) 2-(2-(oxiran-2-yl)ethyl)isoindoline-1,3-dione (A2)

2-(But-3-en-1-yl)isoindoline-1,3-dione A1 (4.31 g, 21.4 mmol), chloroform (50 mL) and mCPBA (70-75%, 6.34 g, 26 mmol @70%) were stirred at room temperature. After 20 hours the mixture was diluted with 10% w/v aqueous sodium thiosulfate solution (100 mL) and stirred vigorously for five minutes. The mixture was diluted with saturated aqueous sodium bicarbonate (100 mL), the organic layer separated and the aqueous layer extracted with chloroform (2×100 mL). The pooled organic extracts were washed with saturated aqueous sodium bicarbonate (100 mL), brine (100 mL), dried over sodium sulfate and concentrated in vacuo to give the title compound as a white solid (4.60 g, 99% yield). LCMS-B: rt 3.43 min; m/z (positive ion) 218.1 [M+H]$^+$ (c) 2-(4-(3,4-dihydroisoquinolin-2(1H)-yl)-3-hydroxybutyl)isoindoline-1,3-dione (A3)

2-(2-(Oxiran-2-yl)ethyl)isoindoline-1,3-dione A2 (4.60 g, 21.2 mmol), ethanol (100 mL) and 1,2,3,4-tetrahydroisoquinoline (3.18 mL, 25.4 mmol) were stirred at 80° C. After 3.5 hours the mixture was concentrated in vacuo and the residue suspended in cold petroleum benzine (150 mL). The mixture was filtered and the collected solid washed with further petroleum benzine (3×50 mL) and air dried to give the title compound as a white solid (6.54 g, 88% yield). LCMS-B: rt 3.30 min; m/z (positive ion) 351.2 [M+H]$^+$; $^1$H NMR (400 MHz, CDCl$_3$) δ 7.88-7.82 (m, 2H), 7.74-7.68 (m, 2H), 7.17-6.96 (m, 4H), 3.98-3.78 (m, 4H), 3.63 (d, J=14.9 Hz, 1H), 2.98-2.86 (m, 3H), 2.76-2.68 (m, 1H), 2.59-2.47 (m, 2H), 1.85-1.78 (m, 2H).

(d) 4-amino-1-(3,4-dihydroisoquinolin-2(1H)-yl) butan-2-ol (A4)

2-(4-(3,4-dihydroisoquinolin-2(1H)-yl)-3-hydroxybutyl) isoindoline-1,3-dione (6.54 g, 18.7 mmol) and ethanol (200 mL) were brought to reflux and hydrazine hydrate (50-60%, 5.81 mL, 93.3 mmol @50%) added. The mixture was vigorously stirred at reflux for three hours then cooled to room temperature. The mixture was filtered and the collected solids washed with ethanol (2×25 mL). The pooled filtrates were concentrated in vacuo, the residue dissolved in ethanol (100 mL) and again concentrated in vacuo to give the title compound as a yellow oil (4.66 g). LCMS-B, m/z (positive ion) 221.2 [M+H]$^+$

(ii) Lithium 4-((4-(3,4-dihydroisoquinolin-2(1H)-yl)-3-hydroxybutyl)carbamoyl)benzoate (I2)

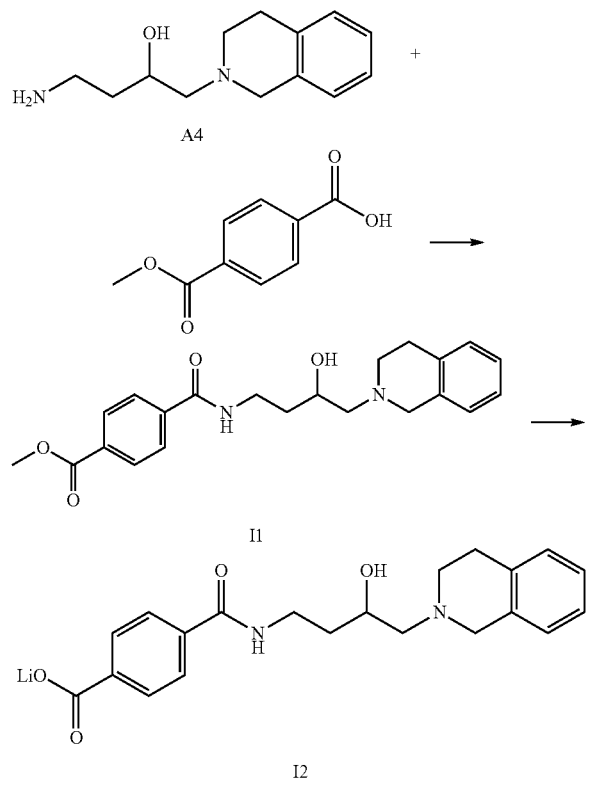

(iii) 4-Methoxy-3-(pyrimidin-5-yl)benzoic Acid (I4)

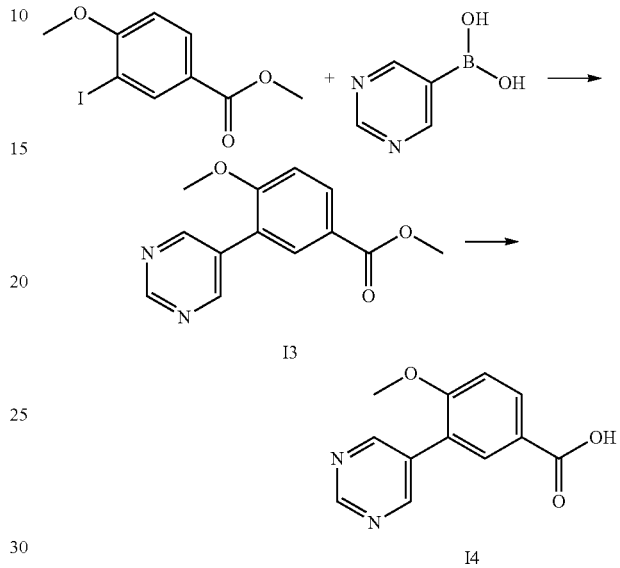

(a) Methyl 4-((4-(3,4-dihydroisoquinolin-2(1H)-yl)-3-hydroxybutyl)carbamoyl)benzoate (I1)

To a solution of 4-amino-1-(3,4-dihydroisoquinolin-2(1H)-yl)butan-2-ol A4 (0.300 g, 1.36 mmol, 1 equiv) in MeCN (20 mL) was added monomethyl terephthalic acid (0.245 g, 1.36 mmol, 1 equiv), DIPEA (712 µL, 4.09 mmol, 3 equiv) and HATU (0.777 g, 2.04 mmol, 1.5 equiv). The reaction was stirred at room temperature for 16 h. The mixture was quenched with a saturated aqueous solution of sodium carbonate (15 mL) and extracted with ethyl acetate (3×30 mL). The pooled organic extracts were washed with water (30 mL), brine (30 mL), dried over magnesium sulfate and evaporated. The crude residue was taken up in MeOH and purified by solid-phase extraction (10 g SCX-2 cartridge, 3 column volumes of methanol followed by 3 column volumes of 0.2 M methanolic ammonia) to give the title compound (215 mg) as a dark yellow solid, containing ~20% of 1-(3,4-dihydroisoquinolin-2(1H)-yl)-4-(4-(methoxycarbonyl)benzamido)butan-2-ylmethyl terephthalate which was used without further purification. LCMS-B: rt=3.16 min, m/z=383 [m+H]+

(b) Lithium 4-((4-(3,4-dihydroisoquinolin-2(1H)-yl)-3-hydroxybutyl)carbamoyl)benzoate (I2)

To a solution of methyl 4-((4-(3,4-dihydroisoquinolin-2(1H)-yl)-3-hydroxybutyl)carbamoyl)benzoate I1 (215 mg, 0.562 mmol, 1 equiv) in H₂O:MeOH (1:2; 20 mL) was added LiOH.H₂O (100 mg, 2.38 mmol, 4 equiv). The reaction was stirred at room temperature for 16 h. The solvent was removed in vacuo to give the title compound (310 mg) as a white solid. LCMS-B: rt 3.14 min, m/z 369 [M+H]+.

(a) Methyl 4-methoxy-3-(pyrimidin-5-yl)benzoate (I3)

A mixture of methyl 3-iodo-4-methoxybenzoate (500 mg, 1.71 mmol), pyrimidin-5-ylboronic acid (318 mg, 2.57 mmol), PdCl₂(dppf).DCM complex (71 mg, 5 mol %), 1,4-dioxane (10 mL) and aqueous 1.0 M Cs₂CO₃ (3.42 mL, 3.42 mmol) was degassed with bubbling nitrogen and heated in the microwave (120° C.130 min). The mixture was added to water (100 mL) and EtOAc (100 mL) and the mixture was filtered through Celite. The filtrate was separated and the aqueous phase was extracted with further EtOAc (100 mL). The pooled organic phases were washed with brine (100 mL), dried over Na₂SO₄ and concentrated. Chromatography (0-80% EtOAc in petroleum benzine 40-60° C.) gave the title product as a white solid (321 mg, 77%). ¹H NMR (400 MHz, d₄-DMSO) δ 9.18 (s, 1H), 8.96 (s, 2H), 8.07 (dd, J=8.7, 2.2 Hz, 1H), 7.97 (d, J=2.2 Hz, 1H), 7.32 (d, J=8.7 Hz, 1H), 3.89 (s, 3H), 3.84 (s, 3H). LCMS-B rt 3.45 min; m/z 245.1 [M+H]+.

(b) 4-methoxy-3-(pyrimidin-5-yl)benzoic Acid (I4)

A suspension of methyl 4-methoxy-3-(pyrimidin-5-yl)benzoate I3 (319 mg, 1.31 mmol) and lithium hydroxide monohydrate (164 mg, 3.92 mmol) in THF (10 mL), MeOH (10 mL) and water (5 mL) was stirred at room temperature. After 18 hours, the mixture was concentrated in vacuo and the aqueous residue diluted to 40 mL with water. The pH was adjusted to 1 with aqueous 6 M HCl, the precipitate collected by filtration, washed with water (10 mL) and dried in vacuo to give the title compound as a white solid (229 mg, 76%). ¹H NMR (400 MHz, d₆-DMSO) δ 9.17 (s, 1H), 8.96 (s, 2H), 8.05 (dd, J=8.7, 2.2 Hz, 1H), 7.94 (d, J=2.2 Hz, 1H), 7.29 (d, J=8.7 Hz, 1H), 3.89 (s, 3H). LCMS-B: rt 3.27 min; m/z 231.1 [M+H]⁺; m/z 229.1 [M−H]⁻.

(iv) 3-(Pyridazin-4-yl)benzoic Acid (I6)

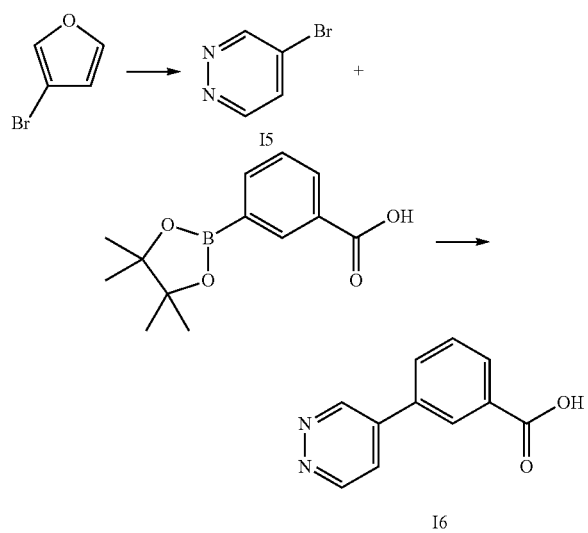

(a) 4-bromopyridazine Hydrobromide (I5)

Potassium acetate (1.84 g, 19 mmol) and 3-bromofuran (0.612 mL, 6.8 mmol) were stirred in acetic acid (5 mL) and a solution of bromine (0.349 mL, 6.8 mmol) in acetic acid (2 mL) was added dropwise. After one hour the mixture was filtered, the solids washed with acetic acid (3 mL) and the filtrate concentrated. The mixture was dissolved in EtOH (10 mL) and hydrazine hydrate (1 mL) added. After 3 hours the mixture was added to EtOAc (50 mL) and the EtOAc washed with brine (2×50 mL). The brine extracts were extracted with EtOAc (50 mL), and the pooled EtOAc extracts dried over Na₂SO₄ and evaporated. The residue was diluted with 1,4-dioxane (5 mL) and treated with 33% HBr in acetic acid (1 mL) dropwise. The dark suspension was filtered, the collected solids washed with 1,4-dioxane (5 mL), acetone (5 mL) and air dried to give the title compound as a brown solid (806 mg, 49% yield). ¹H NMR (400 MHz, d₆-DMSO) δ 9.50 (dd, J=2.6, 1.1 Hz, 1H), 9.14 (dd, J=5.7, 1.0 Hz, 1H), 8.14 (dd, J=5.6, 2.5 Hz, 1H). LCMS-B: rt 2.68 min; m/z 161.0 [M+H]⁺ for ⁸¹Br.

(b) 3-(Pyridazin-4-yl)benzoic Acid (I6)

3-(4,4,5,5-Tetramethyl-1,3,2-dioxaborolan-2-yl)benzoic acid (0.496 g, 2.0 mmol), 4-bromopyridazine hydrobromide I5 (576 mg, 2.4 mmol), PdCl₂(dppf) (83 mg, 5 mol %) and dioxane (10 mL) were loaded into a microwave tube. A solution of potassium carbonate (829 mg, 6.0 mmol) in water (5 mL) was added, the mixture degassed with a stream of nitrogen bubbles then heated in the microwave (120° C./30 minutes). The mixture was cooled, and the volatile solvents removed in vacuo. The aqueous residue was diluted with water to 75 mL, and shaken with DCM (75 mL). The mixture was filtered through celite, the aqueous layer separated and washed with further DCM (75 mL). The DCM extracts were discarded. The aqueous phase was diluted with water (25 mL) and treated with 5% w/v aqueous citric acid solution until pH 3 to pH paper. The resulting precipitate was collected by filtration, washed with water and dried under vacuum to give the title compound as a pale brown solid (312 mg, 78% yield). LCMS-B rt 3.15 min, m/z (positive ion) 201.1 [M+H]⁺; m/z (negative ion) 199.1 [M−H]⁻; ¹H NMR (400 MHz, DMSO) δ 9.70-9.65 (m, 1H), 9.33-9.28 (m, 1H), 8.38 (s, 1H), 8.17 (d, J=7.8 Hz, 1H), 8.12-8.05 (m, 2H), 7.71 (t, J=7.8 Hz, 1H).

(v) 2-((1-acetylpiperidin-4-yl)amino)isonicotinic Acid (I11)

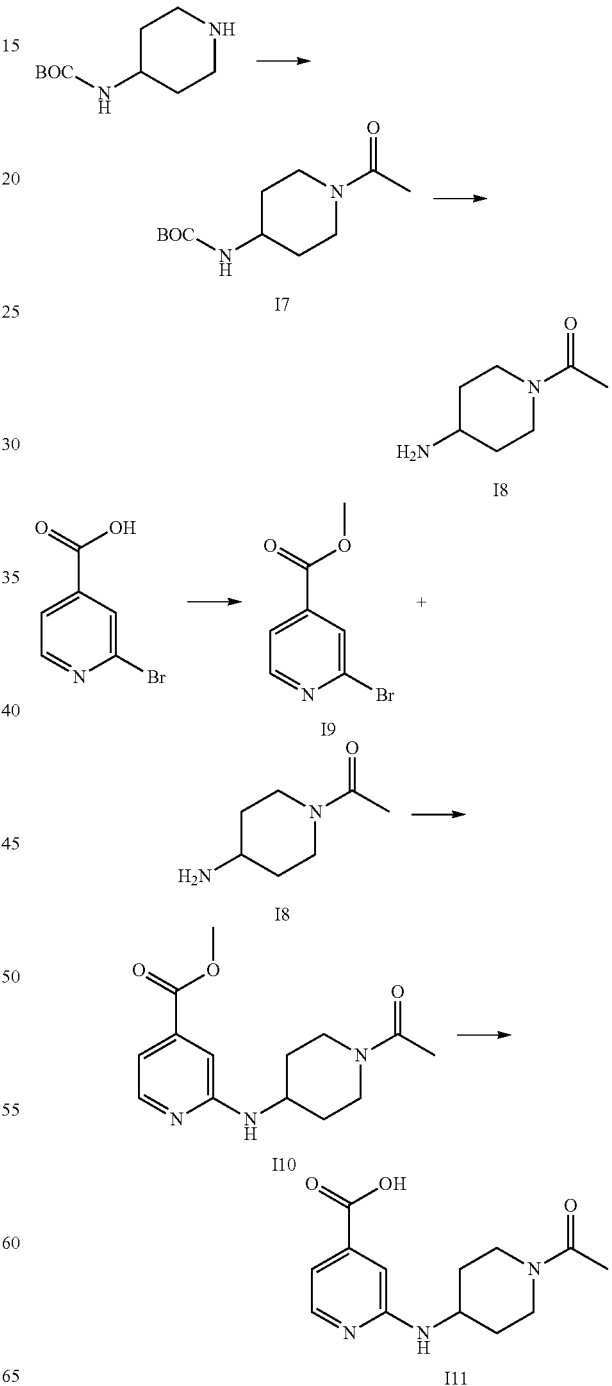

(a) tert-butyl (1-acetylpiperidin-4-yl)carbamate (I7)

Acetic anhydride (4.71 mL, 49.9 mmol) was added to a solution of tert-butyl piperidin-4-ylcarbamate (10.0 g, 49.9 mmol) and triethylamine (10.4 mL, 74.9 mmol) in anhydrous DCM (100 mL) at 0° C. The reaction mixture was stirred at 0° C. for 2 hours before water (~100 mL) and DCM (~50 mL) were added. The organic phase was separated, washed with a saturated aqueous $NaHCO_3$ solution (~100 mL) and dried ($MgSO_4$). The solvent was removed in vacuo to give the title compound as a white solid (10.72 g, 89%). $^1$H NMR (400 MHz, $CDCl_3$) δ 4.54-4.42 (m, 2H), 3.80-3.70 (m, 1H), 3.70-3.58 (m, 1H), 3.12 (ddd, J=14.2, 11.8, 2.9 Hz, 1H), 2.78-2.65 (m, 1H), 2.07 (s, 3H), 2.05-1.97 (m, 1H), 1.96-1.87 (m, 1H), 1.43 (s, 9H), 1.36-1.20 (m, 2H).

(b) 1-(4-aminopiperidin-1-yl)ethan-1-one Hydrochloride (I8)

A solution of tert-butyl (1-acetylpiperidin-4-yl)carbamate I7 (10.72 g, 44.24 mmol) in 1,4-dioxane (100 mL) was cooled to 0° C. and treated with 4.0 M HCl in 1,4-dioxane (12.2 mL, 48.7 mmol). A white precipitate formed following addition of the acid which was isolated by filtration. The precipitate was dissolved in MeOH (100 mL) and treated with 4.0 M HCl in 1,4-dioxane (12.2 mL, 48.7 mmol) and the mixture was stirred at room temperature for 16 hours. Another aliquot of 4.0 M HCl in 1,4-dioxane (6.10 mL, 24.4 mmol) was added and the reaction mixture was stirred for 1.5 hours at 40° C. The volatiles were removed in vacuo and the white solid was dried under high vacuum to give the title compound (8.60 g, ~90% purity, >95% yield). $^1$H NMR (400 MHz, $d_6$-DMSO) δ 8.52-8.23 (m, 3H), 4.39-4.26 (m, 1H), 3.89-3.77 (m, 1H), 3.28-3.14 (m, 1H), 3.11-3.00 (m, 1H), 2.65-2.54 (m, 1H), 1.99 (s, 3H), 1.97-1.86 (m, 2H), 1.54-1.41 (m, 1H), 1.41-1.27 (m, 1H).

(c) Methyl 2-bromoisonicotinate (I9)

A solution of 2-bromoisonicotinic acid (5.00 g, 24.8 mmol) in MeOH (50 mL) was treated with sulfuric acid (0.50 mL, 9.4 mmol) and the reaction mixture was stirred at 80° C. for 1 hour. The mixture was returned to room temperature and stirred for a further 96 hours before heating to 80° C. and stirring for 24 hours. The reaction mixture was cooled to room temperature, and the volatiles were removed in vacuo. An aqueous NaOH solution (2 M, ~50 mL) was added to the residue and the aqueous was extracted with EtOAc (3×50 mL). The organic layers were combined, washed with brine, dried ($MgSO_4$) and the solvent removed in vacuo to give the title compound as a yellow oil (4.14 g, 77%). LCMS-B: rt 3.55 min; m/z 216 [M+H]$^+$ for $^{79}$Br, 218 [M+H]$^+$ for $^{81}$Br; $^1$H NMR (400 MHz, $CDCl_3$) δ 8.52 (dd, J=5.0, 0.8 Hz, 1H), 8.04 (t, J=1.2 Hz, 1H), 7.80 (dd, J=5.0, 1.4 Hz, 1H), 3.96 (s, 3H).

(d) Methyl 2-((1-acetylpiperidin-4-amino)isonicotinate (I10)

A mixture of 1-(4-aminopiperidin-1-yl)ethan-1-one hydrochloride I8 (2.25 g, 12.6 mmol), methyl 2-bromoisonicotinate I9 (1.81 g, 8.38 mmol), $Cs_2CO_3$ (10.92 g, 33.51 mmol), xantphos (0.242 g, 0.419 mmol) and $Pd_2(dba)_3$ (0.384 g, 0.419 mmol) in 1,4-dioxane (40 mL) was bubbled with nitrogen for 10 min. The mixture was then stirred under an atmosphere of nitrogen at 80° C. for 24 hours. Further $Cs_2CO_3$ (5.46 g, 16.8 mmol), xantphos (0.121 g, 0.209 mmol) and $Pd_2(dba)_3$ (0.192 g, 0.210 mmol) were added and the mixture was stirred under an atmosphere of nitrogen at 80° C. for 5 days. The reaction mixture was returned to room temperature and diluted with EtOAc (~150 mL). Solid impurities were removed by filtration and the filtrate solvent was removed in vacuo. The resultant solid was purified by column chromatography (Biotage Isolera, 40 g $SiO_2$ cartridge, 0-100% EtOAc in petroleum benzine 40-60° C., then 0-20% MeOH (containing 1% v/v TEA) in EtOAc) to give the title compound as a yellow solid (0.558 g, 24%). LCMS-B: rt 3.05 min; m/z 278.2 [M+H]$^+$.

(e) 2-((1-acetylpiperidin-4-yl)amino)isonicotinic Acid (I11)

A mixture of methyl 2-((1-acetylpiperidin-4-yl)amino) isonicotinate I10 (0.558 g, 2.01 mmol), LiOH.$H_2O$ (1.69 g, 40.2 mmol), THF (7 mL), MeOH (7 mL) and water (1.5 mL) was stirred at 40° C. for 2 hours. The mixture was returned to room temperature and the volatiles were removed in vacuo. Water (~30 mL) was added and the pH was adjusted to ~6 with an aqueous solution of HCl (2 M). The aqueous phase was passed through an Oasis HLB 35 cc LP extraction cartridge (6 g) which was washed with 4 column volumes of water. The lipophilic component was then eluted with 4 column volumes of MeOH. Evaporation of the MeOH in vacuo gave the title compound as a yellow solid (0.197 g, 37%). The aqueous phase from the first iteration of cartridge purification was passed through another Oasis HLB 35 cc LP extraction cartridge (6 g). The column was washed with 4 column volumes of water and the product was eluted with 4 column volumes of MeOH. Evaporation of the MeOH in vacuo gave further title compound as a white solid (0.128 g, 24%), with NMR data in agreement. Overall yield: 0.325 g, 61%. LCMS-B: rt 1.17 min; m/z 262.1 [M−H]$^−$. $^1$H NMR (400 MHz, $d_6$-DMSO) δ 8.08 (d, J=5.2 Hz, 1H), 6.98 (s, 1H), 6.86-6.79 (m, 2H), 4.26-4.16 (m, 1H), 4.03-3.90 (m, 1H), 3.81-3.72 (m, 1H), 3.21-3.12 (m, 1H), 2.85-2.74 (m, 1H), 2.00 (s, 3H), 1.97-1.83 (m, 2H), 1.41-1.16 (m, 2H).

Example 2

General Procedure A

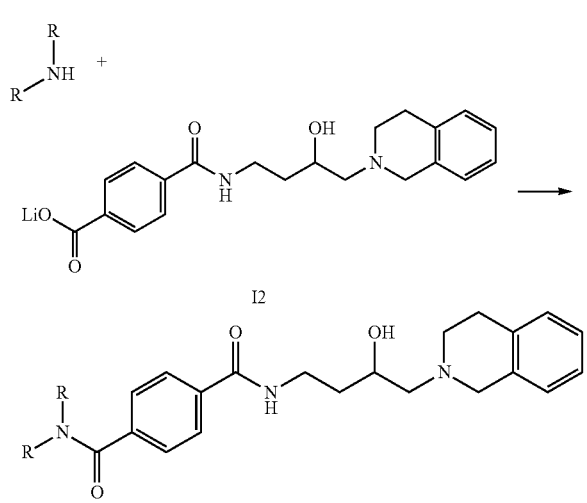

To lithium 4-((4-(3,4-dihydroisoquinolin-2(1H)-yl)-3-hydroxybutyl)carbamoyl)benzoate I2 (70 mg, 0.19 mmol, 1 equiv) in CH₃CN (2 mL) was added DIPEA (130 μL, 0.75 mmol, 4 equiv) and HATU (107 mg, 0.281 mmol, 1.5 equiv). The desired amine (0.561 mmol, 3 equiv) in DMF (1 mL) was added and the reaction stirred at room temperature for 16 h. The reactions were quenched by the addition of a 1M aqueous solution of NaOH (2 mL) and stirred for 1 h. DCM (3 mL) was added, the layers mixed thoroughly and then passed through a phase separation cartridge (3 mL). The aqueous layer was further extracted with DCM utilising the phase separation cartridge (2×3 mL). The combined organic layers were concentrated by a stream of air. An equivalent volume of MeOH was added and the solution purified by solid-phase extraction (1 g SCX-2 cartridge, 3 column volumes of methanol followed by 3 column volumes of 0.2 M methanolic ammonia). The organic solvent was removed in vacuo to give the title compound. Where specified, the compound was further purified by column chromatography (12 g, 50-100% EtOAc (modified by the addition of 1% v/v of 3.5 M methanolic ammonia) in petroleum benzine followed by 0-20% MeOH in EtOAc modified by the addition of 1% v/v of 2.0 M methanolic ammonia) to give the title compound.

General Procedure B

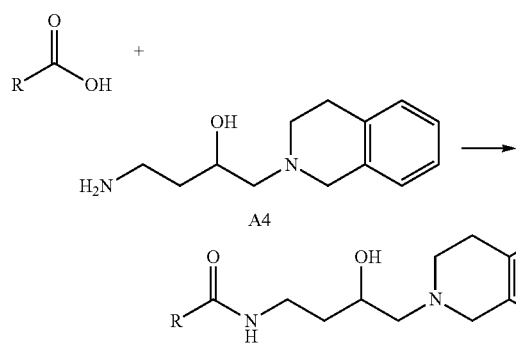

To the acid (0.23 mmol, 1 equiv) in CH₃CN (2 mL) was added DIPEA (120 μL, 0.69 mmol, 3 equiv) and HATU (131 mg, 0.345 mmol, 1.5 equiv). 4-amino-1-(3,4-dihydroisoquinolin-2(1H)-yl)butan-2-ol A4 (51 mg, 0.23 mmol, 1 equiv) in DMF (1 mL) was added and the reaction stirred at room temperature for 16 h. The reactions were quenched by the addition of a 1M solution of NaOH (2 mL) and the stirred for 3 h. DCM (3 mL) was added, the layers mixed thoroughly and then passed through a phase separation cartridge (3 mL). The aqueous layers were further extracted with DCM (3 mL) and the organic layers collected by passage through a phase separation cartridge (2 repeats). The DCM layers were concentrated by a stream of air. An equivalent volume of MeOH was added and the solution purified by solid-phase extraction (1 g SCX-2 cartridge, 3 column volumes of methanol followed by 3 column volumes of 0.2 M methanolic ammonia). The organic solvent was removed in vacuo to give the title compounds.

General Procedure C

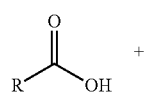

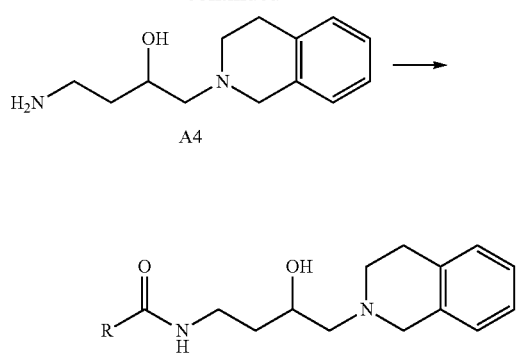

The acid (0.20 mmol) and triethylamine (0.084 mL, 0.60 mmol) were dissolved in DCM. The mixture was cooled to 0° C. and a 1.0 M solution of isopropyl chloroformate in toluene (0.20 mL, 0.20 mmol) added. The mixture was stood for thirty minutes then a 0.40 M solution of 4-amino-1-(3,4-dihydroisoquinolin-2(1H)-yl)butan-2-ol A4 in DCM (0.50 mL, 0.20 mmol) added. The mixtures were stood at room temperature for 17 hours then diluted with methanol (1 mL). The mixtures were loaded onto 2 g SCX cartridges, washed with methanol (15 mL) and eluted with 3.5 M ammonia in methanol (15 mL). The basic eluates were concentrated to give the amide products.

General Procedure D:

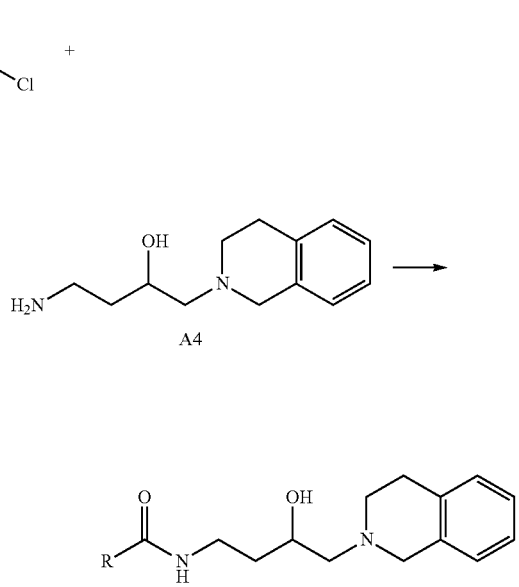

The acyl chlorides (0.20 mmol each) and triethylamine (0.084 mL, 0.60 mmol) were dissolved in DCM (1 mL). A 0.40 M solution of 4-amino-1-(3,4-dihydroisoquinolin-2 (1H)-yl)butan-2-ol A4 in DCM (0.50 mL, 0.20 mmol) was added. The mixtures were stood at room temperature for 17 hours then diluted with methanol (1 mL). The mixtures were loaded onto 2 g SCX cartridges, washed with methanol (15 mL) and eluted with 3.5 M ammonia in methanol (15 mL). The basic eluates were concentrated to give the amide products.

| Cpd | Structure | Analytical Data | Method |
|---|---|---|---|
| 2 | N-(4-(3,4-dihydroisoquinolin-2(1H)-yl)-3-hydroxybutyl)-4-((trifluoromethyl)sulfonyl)benzamide | LCMS-B: rt 3.54 min; m/z 457.2 [M + H]+ | C |
| 3 | N-(4-(3,4-dihydroisoquinolin-2(1H)-yl)-3-hydroxybutyl)-4-((trifluoromethyl)sulfinyl)benzamide | LCMS-B: rt 3.30 min; m/z 441.2 [M + H]+ | C |
| 4 | N-(4-(3,4-dihydroisoquinolin-2(1H)-yl)-3-hydroxybutyl)-2-(2-(methylsulfonyl)phenoxy)acetamide | LCMS-B rt 3.10 min; m/z 433.3 [M + H]+ | C |
| 5 | N-(4-(3,4-dihydroisoquinolin-2(1H)-yl)-3-hydroxybutyl)-4-(trifluoromethyl)benzamide | LCMS-B: rt 3.39 min; m/z 393.2 [M + H]+ | C |
| 6 | N-(4-(3,4-dihydroisoquinolin-2(1H)-yl)-3-hydroxybutyl)-4-(2-oxopiperidin-1-yl)benzamide | LCMS-B: rt 3.18 min; m/z 422.3 [M + H]+ | C |

| Cpd | Structure | Analytical Data | Method |
|---|---|---|---|
| 7 | 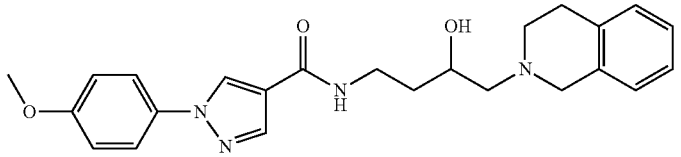<br>N-(4-(3,4-dihydroisoquinolin-2(1H)-yl)-3-hydroxybutyl)-1-(4-methoxyphenyl)-1H-pyrazole-4-carboxamide | LCMS-B: rt 3.32 min; m/z 421.3 [M + H]$^+$ | C |
| 8 | 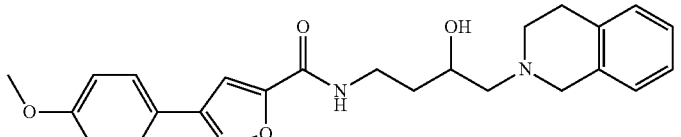<br>N-(4-(3,4-dihydroisoquinolin-2(1H)-yl)-3-hydroxybutyl)-3-(4-methoxyphenyl)isoxazole-5-carboxamide | LCMS-B: rt 3.49 min; m/z 422.3 [M + H]$^+$ | C |
| 9 | 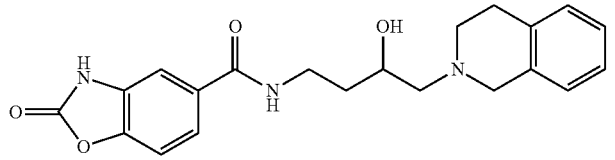<br>N-(4-(3,4-dihydroisoquinolin-2(1H)-yl)-3-hydroxybutyl)-2-oxo-2,3-dihydrobenzo[d]oxazole-5-carboxamide | LCMS-B: rt 3.16 min; m/z 382.3 [M + H]$^+$ | C |
| 10 | 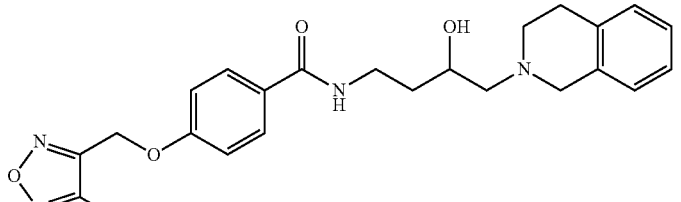<br>N-(4-(3,4-dihydroisoquinolin-2(1H)-yl)-3-hydroxybutyl)-4-((4-methyl-1,2,5-oxadiazol-3-yl)methoxy)benzamide | LCMS-B: rt 3.34 min; m/z 437.3 [M + H]$^+$ | C |
| 11 | 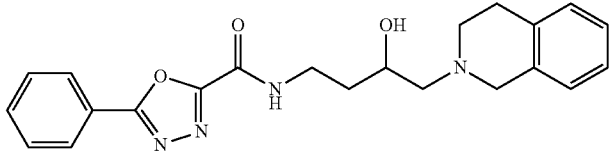<br>N-(4-(3,4-dihydroisoquinolin-2(1H)-yl)-3-hydroxybutyl)-5-phenyl-1,3,4-oxadiazole-2-carboxamide | LCMS-B: rt 3.31 min; molecular ion not detected | C |

-continued

| Cpd | Structure | Analytical Data | Method |
|---|---|---|---|
| 12 | 1-benzyl-N-(4-(3,4-dihydroisoquinolin-2(1H)-yl)-3-hydroxybutyl)-2-oxo-1,2-dihydropyridine-4-carboxamide | LCMS-B: 3.23 min; m/z 432.3 [M + H]$^+$ | C |
| 13 | N-(4-(3,4-dihydroisoquinolin-2(1H)-yl)-3-hydroxybutyl)-5-methyl-1-(pyridin-4-yl)-1H-pyrazole-4-carboxamide | LCMS-B: 3.10 min; m/z 406.3 [M + H]$^+$ | C |
| 14 | N-(4-(3,4-dihydroisoquinolin-2(1H)-yl)-3-hydroxybutyl)-6-morpholinonicotinamide | LCMS-B: 3.02 min; m/z 411.3 [M + H]$^+$ | C |
| 15 | 4-cyano-N-(4-(3,4-dihydroisoquinolin-2(1H)-yl)-3-hydroxybutyl)benzamide | LCMS-B: 3.19 min; m/z 305.2 [M + H]$^+$ | C |
| 16 | 3-cyano-N-(4-(3,4-dihydroisoquinolin-2(1H)-yl)-3-hydroxybutyl)benzamide | LCMS-B: 3.22 min; m/z 350.3 [M + H]$^+$ | C |
| 17 | N-(4-(3,4-dihydroisoquinolin-2(1H)-yl)-3-hydroxybutyl)nicotinamide | LCMS-B: 3.05 min; m/z 326.2 [M + H]$^+$ | C |

-continued

| Cpd | Structure | Analytical Data | Method |
|---|---|---|---|
| 18 | 3-chloro-N-(4-(3,4-dihydroisoquinolin-2(1H)-yl)-3-hydroxybutyl)benzamide | LCMS-B: 3.26 min; m/z 359.2 [M + H]$^+$ | C |
| 19 | N-(4-(3,4-dihydroisoquinolin-2(1H)-yl)-3-hydroxybutyl)-4-(trifluoromethoxy)benzamide | LCMS-B: 3.46 min; m/z 409.3 [M + H]$^+$ | D |
| 20 | N-(4-(3,4-dihydroisoquinolin-2(1H)-yl)-3-hydroxybutyl)-4-(pentafluoro-$\lambda^6$-sulfonyl)benzamide | LCMS-B: 3.48 min; m/z 451.2 [M + H]$^+$ | D |
| 21 | 4-(difluoromethoxy)-N-(4-(3,4-dihydroisoquinolin-2(1H)-yl)-3-hydroxybutyl)benzamide | LCMS-B: 3.36 min; m/z 391.3 [M + H]$^+$ | C |
| 22 | N-(4-(3,4-dihydroisoquinolin-2(1H)-yl)-3-hydroxybutyl)-4-(methylsulfonyl)benzamide | LCMS-B: 3.21 min; m/z 403.3 [M + H]$^+$ | C |

| Cpd | Structure | Analytical Data | Method |
|---|---|---|---|
| 23 | 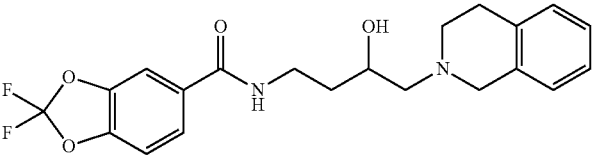<br>N-(4-(3,4-dihydroisoquinolin-2(1H)-yl)-3-hydroxybutyl)-2,2-difluorobenzo[d][1,3]dioxole-5-carboxamide | LCMS-B: 3.58 min; m/z 405.2 [M + H]$^+$ | C |
| 24 | 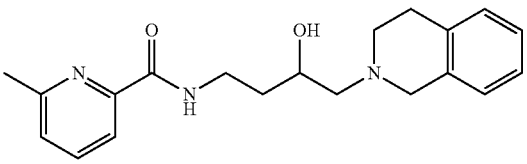<br>N-(4-(3,4-dihydroisoquinolin-2(1H)-yl)-3-hydroxybutyl)-6-methylpicolinamide | LCMS-B: 3.27 min; m/z 340.2 [M + H]$^+$ | C |
| 25 | 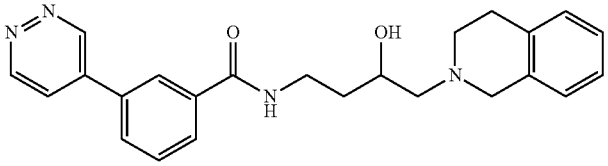<br>N-(4-(3,4-dihydroisoquinolin-2(1H)-yl)-3-hydroxybutyl)-3-(pyridazin-4-yl)benzamide | LCMS-B: 3.19 min; m/z 403.3 [M + H]$^+$ | C, From I6 |
| 26 | 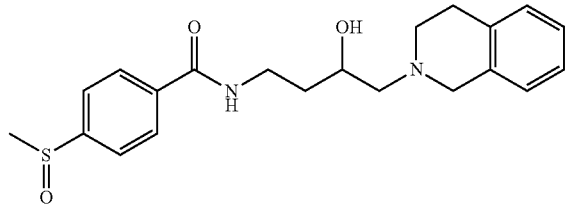<br>N-(4-(3,4-dihydroisoquinolin-2(1H)-yl)-3-hydroxybutyl)-4-(methylsulfinyl)benzamide | LCMS-B: 3.13 min; m/z 387.2 [M + H]$^+$ | C |
| 27 | 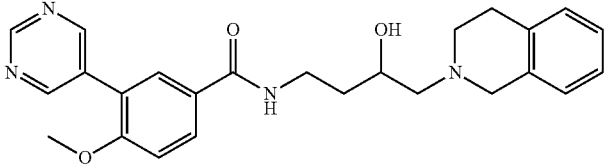<br>N-(4-(3,4-dihydroisoquinolin-2(1H)-yl)-3-hydroxybutyl)-4-methoxy-3-(pyrimidin-5-yl)benzamide | LCMS-B: 3.21, 3.26 min; m/z 433.3 [M + H]$^+$ | C, From I4 |
| 28 | 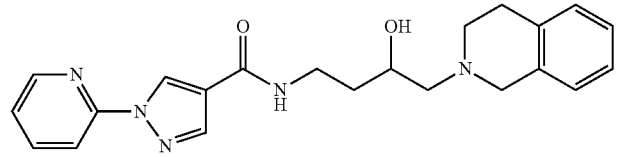<br>N-(4-(3,4-dihydroisoquinolin-2(1H)-yl)-3-hydroxybutyl)-1-(pyridin-2-yl)-1H-pyrazole-4-carboxamide | LCMS-B: 3.20 min; m/z 392.3 [M + H]$^+$ | C |

| Cpd | Structure | Analytical Data | Method |
|---|---|---|---|
| 29 | N-(4-(3,4-dihydroisoquinolin-2(1H)-yl)-3-hydroxybutyl)-1-methyl-2-oxo-1,2-dihydropyridine-4-carboxamide | LCMS-B: 3.09 min; m/z 356.3 [M + H]$^+$ | C, except on a 0.25 mmol scale |
| 30 | N-(4-(3,4-dihydroisoquinolin-2(1H)-yl)-3-hydroxybutyl)-4-(pyrrolidine-1-carbonyl)benzamide | LCMS-B: rt 3.20 min, m/z 422.3 [M + H]$^+$. | A Compound was subjected to column chromatography |
| 31 | 4-(azetidine-1-carbonyl)-N-(4-(3,4-dihydroisoquinolin-2(1H)-yl)-3-hydroxybutyl)benzamide | LCMS-B: rt 3.14 min, m/z 408.3 [M + H]$^+$. | A |
| 32 | $N^1$-(4-(3,4-dihydroisoquinolin-2(1H)-yl)-3-hydroxybutyl)-$N^4$,$N^4$-dimethylterephthalamide | LCMS-B: rt 3.13 min, m/z 396.3 [M + H]$^+$. | A Compoun was subjected to column chromatography |
| 33 | N-(4-(3,4-dihydroisoquinolin-2(1H)-yl)-3-hydroxybutyl)-5-methyl-1-(pyridin-2-yl)-1H-pyrazole-4-carboxamide | LCMS-B: rt 3.21 min, m/z 406 [M + H]$^+$. | B |

| Cpd | Structure | Analytical Data | Method |
|---|---|---|---|
| 34 | 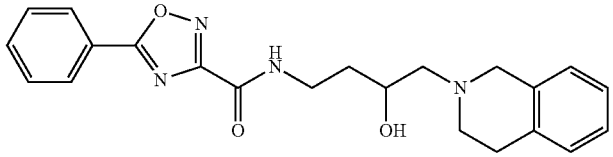<br>N-(4-(3,4-dihydroisoquinolin-2(1H)-yl)-3-hydroxybutyl)-5-phenyl-1,2,4-oxadiazole-3-carboxamide | LCMS-B: rt 3.34 min, m/z 393 [M + H]$^+$. | B |
| 35 | 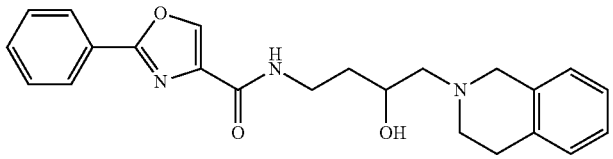<br>N-(4-(3,4-dihydroisoquinolin-2(1H)-yl)-3-hydroxybutyl)-2-phenyloxazole-4-carboxamide | LCMS-B: rt 3.31 min, m/z 392 [M + H]$^+$. | B |
| 36 | 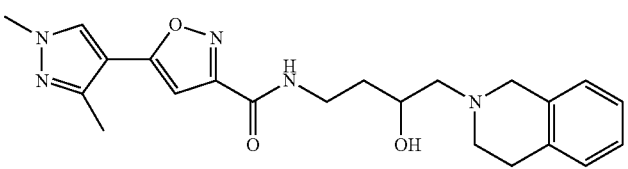<br>N-(4-(3,4-dihydroisoquinolin-2(1H)-yl)-3-hydroxybutyl)-5-(1,3-dimethyl-1H-pyrazol-4-yl)isoxazole-3-carboxamide | LCMS-B: rt 3.17 min, m/z 410 [M + H]$^+$. | B |
| 37 | 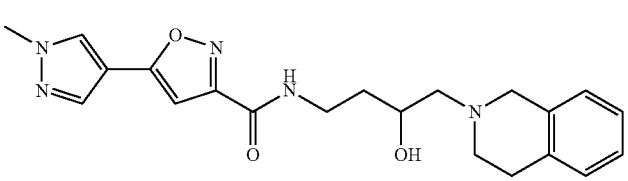<br>N-(4-(3,4-dihydroisoquinolin-2(1H)-yl)-3-hydroxybutyl)-5-(1-methyl-1H-pyrazol-4-yl)isoxazole-3-carboxamide | LCMS-B: rt 3.16 min, m/z 396 [M + H]$^+$. | B |
| 38 | 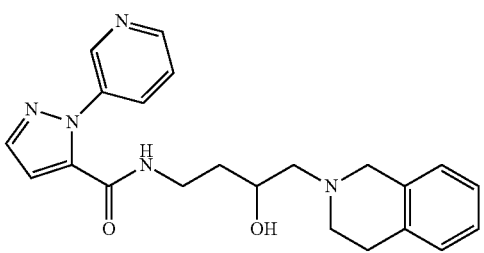<br>N-(4-(3,4-dihydroisoquinolin-2(1H)-yl)-3-hydroxybutyl)-1-(pyridin-3-yl)-1H-pyrazole-5-carboxamide | LCMS-B: rt 3.13 min, m/z 392 [M + H]$^+$. | B |

-continued

| Cpd | Structure | Analytical Data | Method |
|---|---|---|---|
| 39 | 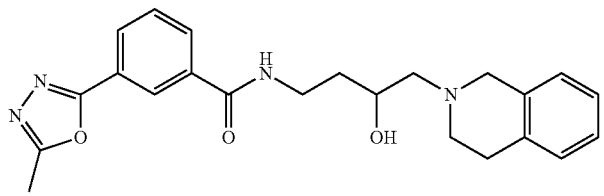<br>N-(4-(3,4-dihydroisoquinolin-2(1H)-yl)-3-hydroxybutyl)-3-(5-methyl-1,3,4-oxadiazol-2-yl)benzamide | LCMS-B: rt 3.22 min, m/z 407 [M + H]$^+$. | B |
| 40 | 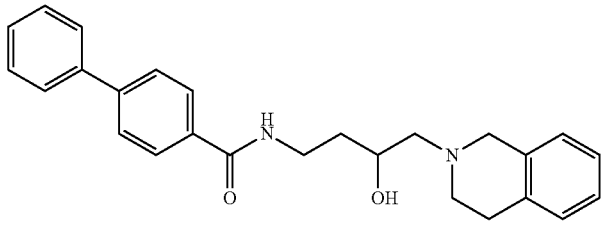<br>N-(4-(3,4-dihydroisoquinolin-2(1H)-yl)-3-hydroxybutyl)-[1,1'-biphenyl]-4-carboxamide | LCMS-B: rt 3.47 min, m/z 401 [M + H]$^+$. | B |
| 41 | 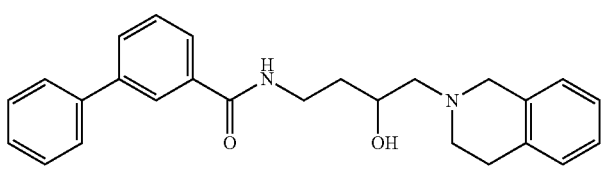<br>N-(4-(3,4-dihydroisoquinolin-2(1H)-yl)-3-hydroxybutyl)-[1,1'-biphenyl]-3-carboxamide | LCMS-B: rt 3.48 min, m/z 401 [M + H]$^+$. | B |
| 42 | 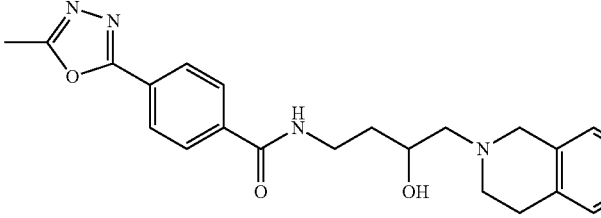<br>N-(4-(3,4-dihydroisoquinolin-2(1H)-yl)-3-hydroxybutyl)-4-(5-methyl-1,3,4-oxadiazol-2-yl)benzamide | LCMS-B: rt 3.18 min, m/z 407 [M + H]$^+$. | B |
| 43 | 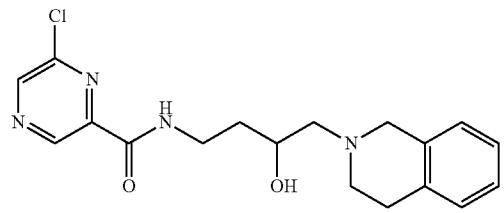<br>6-chloro-N-(4-(3,4-dihydroisoquinolin-2(1H)-yl)-3-hydroxybutyl)pyrazine-2-carboxamide | LCMS-B: rt 3.18 min, m/z 361 [M + H]$^+$. | B |

Example 3: 2-Chloro-N-(4-(3,4-dihydroisoquinolin-2(1H)-yl)-3-hydroxybutyl)isonicotinamide 44

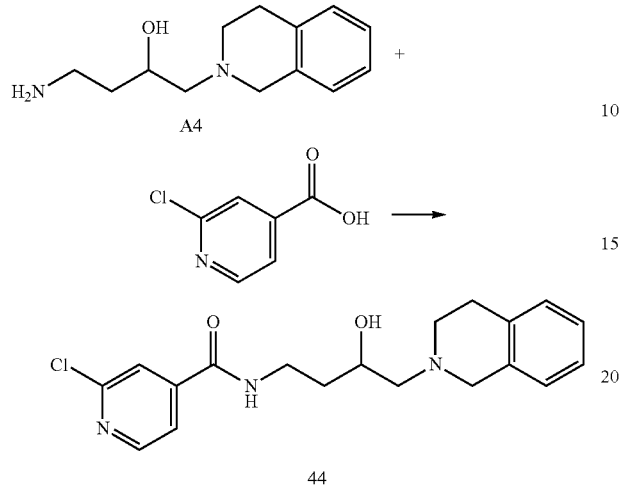

To 2-chloroisonicotinic acid (0.23 mmol, 1 equiv) in CH₃CN (2 mL) was added DIPEA (120 μL, 0.69 mmol, 3 equiv) and HATU (131 mg, 0.345 mmol, 1.5 equiv). 4-amino-1-(3,4-dihydroisoquinolin-2(1H)-yl)butan-2-ol A4 (51 mg, 0.23 mmol, 1 equiv) in DMF (1 mL) was added and the reaction stirred at room temperature for 16 h. The reaction was quenched by the addition of a 1M aqueous solution of NaOH (2 mL) and then stirred for 3 h. The reaction was extracted with DCM (3×3 mL) utilising a phase separation cartridge and the combined organic layers reduced under a stream of air. An equivalent volume of MeOH was added and the solution purified by solid-phase extraction (1 g SCX-2 cartridge, 3 column volumes of methanol followed by 3 column volumes of 0.2 M methanolic ammonia). The organic solvent was removed in vacuo and the residue was purified by column chromatography (12 g, 50-100% EtOAc (modified by the addition of 1% v/v of 3.5 M methanolic ammonia) in petroleum benzine followed by 0-50% MeOH in EtOAc modified by the addition of 1% v/v of 2.0 M methanolic ammonia) to give the title compound as a pale yellow oil (8 mg, 10% yield). $^1$H NMR (400 MHz, MeOD) δ 8.47 (dd, J=5.2, 0.7 Hz, 1H), 7.80 (dd, J=1.5, 0.7 Hz, 1H), 7.68 (dd, J=5.1, 1.5 Hz, 1H), 7.15-7.06 (m, 3H), 7.05-6.95 (m, 1H), 4.03-3.91 (m, 1H), 3.81-3.66 (m, 2H), 3.62-3.48 (m, 2H), 3.00-2.82 (m, 4H), 2.70-2.54 (m, 2H), 1.96-1.82 (m, 1H), 1.78-1.63 (m, 1H).

Example 4: N-(4-(3,4-dihydroisoquinolin-2(1H)-yl)-3-hydroxybutyl)-3-(morpholine-4-carbonyl)benzamide 45

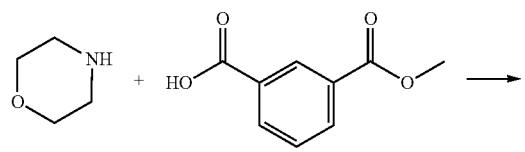

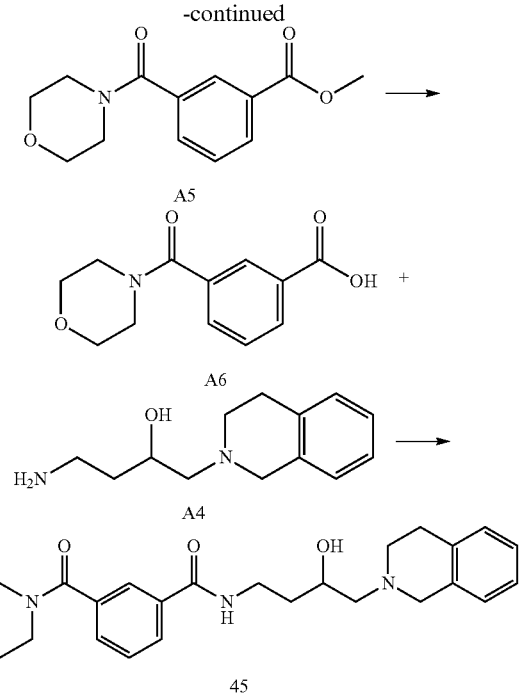

(a) Methyl 3-(morpholine-4-carbonyl)benzoate A5

Morpholine (958 μL, 11.1 mmol, 1 equiv), mono-methyl isophthalate (2.00 g, 11.1 mmol, 1 equiv), MeCN (50 mL), DIPEA (5.80 mL, 33.3 mmol, 3 equiv) and HATU (4.64 g, 12.2 mmol, 1.1 equiv) were stirred at room temperature. After two hours the mixture was quenched with 5% w/v aqueous sodium carbonate (50 mL) and the organic solvents removed in vacuo. The aqueous residue was extracted with ethyl acetate (3×50 mL), and the pooled organic extracts washed with water (2×50 mL), dried over sodium sulfate and evaporated. Chromatography (40 g silica cartridge, 0-50% ethyl acetate in petroleum benzine) and collection of the suspected product fractions gave the title compound (2.718 g, 98% yield) as a pale brown oil. LCMS-B: rt 3.32 min, m/z 250 [M+H]⁺.

(b) 3-(Morpholine-4-carbonyl)benzoic Acid A6

LiOH.H₂O (1.37 g, 32.7 mmol, 3 equiv) was added to a solution of Methyl 3-(morpholine-4-carbonyl)benzoate A5 (2.72 g, 10.9 mmol) in MeOH (20 mL) and water (10 mL) and the resulting suspension was stirred for 16 hours at room temperature. The volatiles were removed in vacuo to give a white solid. Water was added, followed by a 0.5 M aqueous solution of citric acid until the solution was at pH 4. The mixture was stirred for 30 minutes before it was extracted with EtOAc (3×70 mL). The combined organic layers were washed with brine (100 mL), dried (MgSO₄) and concentrated in vacuo to give the title compound (1.74 g, 68% yield) as a white solid. LCMS-B: rt 3.19 min, m/z 236 [m+H]⁺, 234 [M−H]⁻.

(c) N-(4-(3,4-dihydroisoquinolin-2(1H)-yl)-3-hydroxybutyl)-3-(morpholine-4-carbonyl)benzamide 45

3-(Morpholine-4-carbonyl)benzoic acid A6 (54 mg, 0.23 mmol, 1 equiv) in CH₃CN (2 mL) was added DIPEA (120

µL, 0.69 mmol, 3 equiv) and HATU (131 mg, 0.345 mmol, 1.5 equiv). 4-amino-1-(3,4-dihydroisoquinolin-2(1H)-yl)butan-2-ol A4 (51 mg, 0.23 mmol, 1 equiv) in DMF (1 mL) was added and the reaction stirred at room temperature for 16 h. The reaction was quenched by the addition of a 1M aqueous solution of NaOH (2 mL) and then stirred for 3 h. DCM (3 mL) was added, the layers mixed thoroughly and then passed through a phase separation cartridge (3 mL). The aqueous layer was further extracted with DCM (3 mL) and the organic layers collected by passage through a phase separation cartridge (2 repeats). The combined DCM layers were concentrated by a stream of air. An equivalent volume of MeOH was added and the solution purified by solid-phase extraction (1 g SCX-2 cartridge, 3 column volumes of methanol followed by 3 column volumes of 0.2 M methanolic ammonia). The crude material was purified by column chromatography (12 g $SiO_2$ cartridge, 60-100% EtOAc (modified by the addition of 1% v/v 3.5 M methanolic ammonia) in petroleum benzine followed by 0-20% methanol in EtOAc (modified by the addition of 1% v/v 3.5 M methanolic ammonia) to give the title compound. LCMS-B: rt 3.16 min, m/z 438.3 [M+H]$^+$.

Example 5: 24(1-acetylpiperidin-4-yl)amino)-N-(4-(3,4-dihydroisoquinolin-2(1H)-yl)-3-hydroxybutyl) isonicotinamide 46

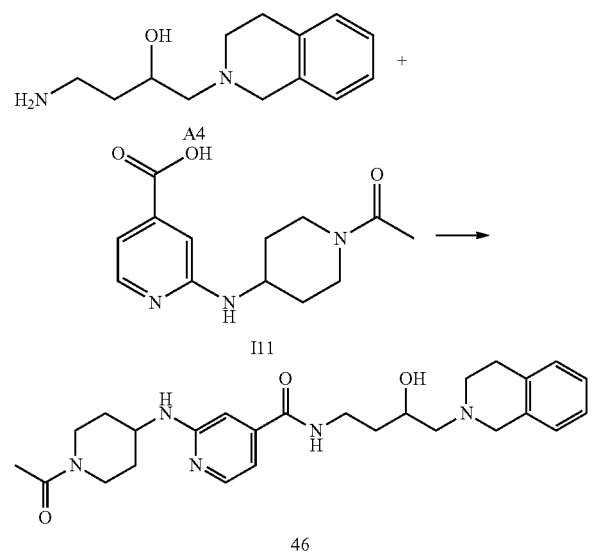

2-((1-Acetylpiperidin-4-yl)amino)isonicotinic acid I11 (30 mg, 0.115 mmol, 1 equiv) and triethylamine (0.096 mL, 0.69 mmol) were dissolved in DCM. The mixture was cooled to 0° C. and a 1.0 M solution of isopropyl chloroformate in toluene (0.23 mL, 0.23 mmol) added. The mixture was stood for thirty minutes then a 0.40 M solution of 4-amino-1-(3,4-dihydroisoquinolin-2(1H)-yl)butan-2-ol A4 in DCM (0.50 mL, 0.20 mmol) added. The mixture stood at room temperature for 17 hours and was then diluted with methanol (1 mL), loaded onto a 2 g SCX cartridge, washed with methanol (15 mL) and eluted with 3.5 M ammonia in methanol (15 mL). The basic eluent was concentrated and purified by column chromatography (12 g $SiO_2$ cartridge, 60-100% EtOAc (modified by the addition of 1% v/v 3.5 M methanolic ammonia) in petroleum benzine followed by 0-45% methanol in EtOAc (modified by the addition of 1% v/v 3.5 M methanolic ammonia) to give the title compound as a colourless oil. LCMS-B: rt 3.03 min, m/z 466.3 [M+H]$^+$.

Assays

PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-$NH_2$). Full-length PRMT5 enzyme (NCBI Reference sequence NP_006100.2) was co-expressed with Hiss-MEP50 in insect cells and purified via Nickel immobilized metal affinity and gel filtration chromatography ("the enzyme").

The κ µL assay reactions are run in Greiner brand black 384-well low volume plates. All reactions contained assay buffer (phosphate buffered saline, 0.01% (v/v) Tween-20, 0.01% (w/v) albumin from chicken egg white, 1 mM dithiothreitol, 200 nM peptide substrate, 1 µM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37° C. Reaction progress was measured using the Transcreener™ EPIGEN methyltransferase assay (BellBrook Labs, Madison, Wis.) as recommended by the manufacturer. To each reaction 2 µL detection mix were added, containing coupling enzymes, fluorescence polarisation tracer, and AMP antibody. Plates were incubated for 90 min before being read on a PerkinElmer EnVision™ plate reader in fluorescence polarisation mode. $IC_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % 1 data vs. compound concentration [I] to % I=(A+((B−A)/(1+((C/[I])^D)))) where A is the lower asymptote, B is the upper asymptote, C is the $IC_{50}$ value, and D is the slope.

| Example Number | $IC_{50}$ (µM) |
|---|---|
| 1 | 0.359 |

PRMT5 Biomarker Assay

Compounds of the invention may be tested for potency to inhibit symmetrical demethylation of arginine in the following assay:

The cell line TE11 was seeded at a density of 12,000 cells per well in 96 well tissue culture plates in DME medium and 10% foetal bovine serum, and allowed to adhere overnight under standard culture conditions (37° C., 5% $CO_2$). Compound dilutions prepared in DMSO were added to the medium, with negative control wells reserved for treatment with DMSO only and positive controls receiving a potent PRMT5 inhibitor. The concentration of the inhibitor had been previously determined to give maximum inhibition of the methylation. After incubation for 72 h, cells were washed twice in ice-cold PBS, lysed in lysis buffer (20 mM Tris pH 7.4, 135 mM NaCl, 1.5 mM $MgCl_2$, 1 mM EGTA, 10% glycerol and 1% Triton-X100), centrifuged at 15,000×g and the supernatants collected for subsequent analysis. The methylation level was determined using the EpiQuik™ Global Di-Methyl Histone H4R3 Quantification ELISA Kit (Epigentek, Farmingdale, N.Y.) as per the manufacturer's recommendations; in parallel the total protein amount in the lysate was quantified using a Lowry protein assay. The methylation level was corrected for the total protein amount of each sample, normalised to the controls, and the data fitted against a four-parameter logistic model to determine the 50% inhibitory concentration ($IC_{50}$).

| Compound Number | $IC_{50}$ (µM) |
|---|---|
| 1 | 0.0404 |

Revised PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-$NH_2$). Full-length PRMT5 enzyme (NCBI Reference sequence NP_006100.2) was co-expressed with Hiss-MEP50 in insect cells and purified via Nickel immobilized metal affinity and gel filtration chromatography ("the enzyme").

The 6 µL reactions are run in Greiner brand black 384-well low volume assay plates. All reactions contained assay buffer (phosphate buffered saline, 0.01% (v/v) Tween-20, 0.01% (w/v) albumin from chicken egg white, 1 mM Dithiothreitol, 1 µM peptide substrate, 1 µM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37 degree Celsius. Reaction progress was measured using the Transcreener™ EPIGEN methyltransferase assay (Bell-Brook Labs, Madison, Wis.) as recommended by the manufacturer. To each reaction 2 µL detection mix were added, containing coupling enzymes, fluorescence polarisation tracer, and AMP antibody. Plates were incubated for 90 minutes before being read on a PerkinElmer EnVision™ plate reader in fluorescence polarisation mode. $IC_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the $IC_{50}$ value, and D is the slope.

| Compound Number | $IC_{50}$ (µM) |
|---|---|
| 2 | 1.132 |
| 3 | 0.925 |
| 4 | 51.680 |
| 5 | 1.331 |
| 6 | 13.103 |
| 7 | 1.941 |
| 8 | 3.089 |
| 9 | 4.351 |
| 10 | 3.982 |
| 11 | 39.185 |
| 12 | 1.595 |
| 13 | 7.089 |
| 14 | 0.910 |
| 15 | 3.977 |
| 16 | 13.024 |

-continued

| Compound Number | $IC_{50}$ (µM) |
|---|---|
| 17 | 15.026 |
| 18 | 9.794 |
| 19 | 0.319 |
| 20 | 0.214 |
| 21 | 0.415 |
| 22 | 7.019 |
| 23 | 1.689 |
| 24 | 25.379 |
| 25 | 6.350 |
| 26 | 3.746 |
| 27 | 5.621 |
| 28 | 12.294 |
| 29 | 10.792 |
| 30 | 3.121 |
| 31 | 3.164 |
| 32 | 3.542 |
| 33 | 7.452 |
| 34 | 56.096 |
| 35 | 1.214 |
| 36 | 1.198 |
| 37 | 1.186 |
| 38 | 2.883 |
| 39 | 1.220 |
| 40 | 0.769 |
| 41 | 5.286 |
| 42 | 2.834 |
| 43 | 105.667 |
| 44 | 13.686 |
| 45 | 5.228 |
| 46 | 0.186 |

Revised PRMT5 Biomarker Assay

Compounds of the invention may be tested for potency to inhibit symmetrical dimethylation of arginine in the following assay:

The cell line TE11 was seeded at a density of 6,000 cells per well in 96 well optical quality tissue culture plates in DME medium and 10% foetal bovine serum, and allowed to adhere for 5 hours under standard culture conditions (37 degree Celsius, 5% $CO_2$). Compound dilutions prepared in DMSO were added to the medium, with negative control wells reserved for treatment with DMSO only and positive controls receiving a potent PRMT5 inhibitor compound at 1 µM concentration. After incubation for 72 hours, the cells were fixed with 3.7% formaldehyde in PBS for 30 minutes at room temperature, washed with phosphate buffer saline and blocked with Odyssey blocking buffer (LI-COR, Lincoln, Nebr.). Rabbit anti-Di-Methyl Histone H4 Arginine 3 specific antibody (Epigentek) in Odyssey blocking buffer was added and incubated for 14 hours at 4 degree Celsius. After washing, anti-rabbit secondary antibody labelled with Alexa647 dye (LifeTechnologies) and Hoechst 33342 (1 µg/mL, SigmaAldrich) were added for 1 hour incubation. Plates were washed and read on a PerkinElmer Envision 2103 in fluorescence intensity scanning mode (24 scans across the well area). The methylation level information was corrected for the number of cells as expressed by the Hoechst 33342 stain, converted to percent inhibition relative to controls on the same plate and the data fitted against a four-parameter logistic model to determine the 50% inhibitory concentration ($IC_{50}$ plate-reader based). Alternatively, the plates were imaged on a PerkinElmer Phenix high content imaging platform. Using a Columbus image analysis pipeline, individual nuclei were located by Hoechst 33342 stain and the methylation level was calculated from the Alexa647-related intensity in the same area. The resulting mean intensity per cell was directly converted to percent inhibition as outlined above ($IC_{50}$, imager based)).

| Compound Number | IC$_{50}$ (µM) plate-reader based |
| --- | --- |
| 1 | 0.318 |
| 19 | 0.089 |
| 20 | 0.505 |
| 36 | 0.023 |
| 40 | 0.048 |
| 46 | 0.007 |

The invention claimed is:

1. A compound of formula I:

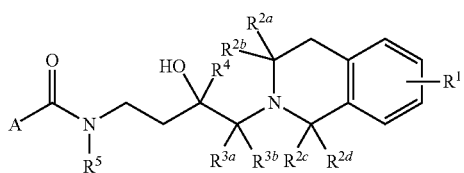

(I)

wherein:

$R^1$ is absent, or one or more halo or methyl groups;

$R^{2a}$ and $R^{2b}$ are independently selected from the group consisting of:
(i) F;
(ii) H;
(iii) Me; and
(iv) CH$_2$OH;

$R^{2c}$ and $R^{2d}$ are independently selected from the group consisting of:
(i) F;
(ii) H;
(iii) Me; and
(iv) CH$_2$OH;

$R^{3a}$ and $R^{3b}$ are independently selected from H and Me;

$R^4$ is either H or Me;

$R^5$ is either H or Me;

A is either
(i) optionally substituted phenyl;
(ii) optionally substituted naphthyl; or
(iii) optionally substituted C$_{5-12}$ heteroaryl;
wherein when A is substituted, the substituents are independently selected from the group consisting of: C1-4 alkyl, C1-4 fluoroalkyl, C3-6 cycloalkyl, C5-6 heteroaryl, C5-6 heteroaryl methyl, C4-6 heterocyclyl, C4-6 heterocyclyl methyl, phenyl, benzyl, halo, amido, amidomethyl, acylamido, acylamidomethyl, C1-4 alkyl ester, C1-4 alkyl ester methyl, C1-4 alkyl carbamoyl, C1 4 alkyl carbamoyl methyl, C1-4 alkylacyl, C1-4 alkylacyl methyl, phenylcarbonyl, carboxy, carboxymethyl, ether, amino, aminomethyl, sulfonamido, sulfonamino, sulfone, sulfoxide, nitrile and nitrilemethyl and when A is phenyl, the optional substituent may also be a fused C5-6 N1-containing heterocyclic ring.

2. A compound according to claim 1, wherein $R^1$ represents one to four Me or halo groups.

3. A compound according to claim 1, wherein:
(a) $R^{2a}$, $R^{2b}$, $R^{2c}$ and $R^{2d}$ are all H; or
(b) $R^{2a}$, $R^{2b}$, $R^{2c}$ and $R^{2d}$ consist of three H and one Me or CH$_2$OH group; or
(c) $R^{2a}$, $R^{2b}$, $R^{2c}$ and $R^{2d}$ consist of two H and two Me groups.

4. A compound according to claim 1, wherein:
(a) $R^{3a}$ is H and $R^{3b}$ is Me; or
(b) $R^{3a}$ and $R^{3b}$ are both H; or
(c) $R^{3a}$ and $R^{3b}$ are both Me.

5. A compound according to claim 1 which is of formula Ia:

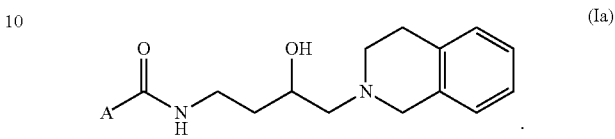

(Ia)

6. A compound according to claim 1, which is a racemate at the carbon atom to which $R^4$ is attached.

7. A compound according to claim 1, which is a single enantiomer at the carbon atom to which $R^4$ is attached.

8. A compound according to claim 1, wherein A is optionally substituted phenyl, wherein the substituents are selected from: C$_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—CN, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted with one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetraydropyanyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$CF$_3$, -γ-lactam, —CH$_2$NHC(=O)Me, —CH$_2$NHC(=O)OMe, —CH$_2$NHC(=O)CF$_3$, morpholino, —CH$_2$NH$_2$, —C(=O)Ph, —OCH$_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

9. A compound according to claim 8, wherein:
(a) in the ortho position of the phenyl group there is a halo or methoxy substituent; or
(b) in the para position of the phenyl group there is an amido or amidomethyl substituent; or
(c) the phenyl group bears a halo or methoxy substituent in the ortho position, and an amido or amidomethyl substituent in the para position of the phenyl group; or
(d) in the meta position of the phenyl group there is an amino substituent.

10. A compound according to claim 1, wherein:
(a) A is optionally substituted naphthyl; or
(b) optionally substituted C$_{5-12}$ heteroaryl selected from the group consisting of: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl.

11. A compound according to claim 1, wherein A is selected from one of the following groups:

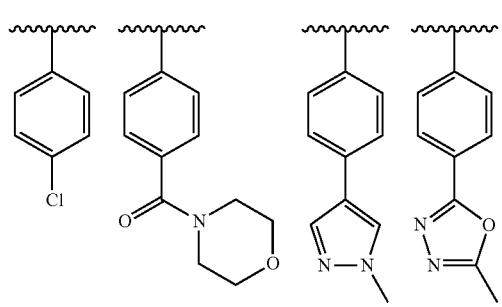
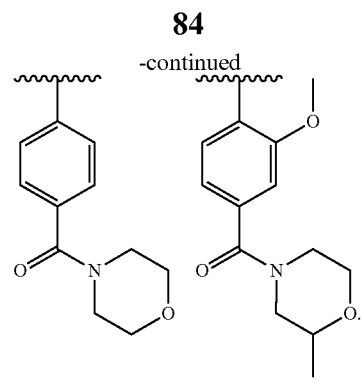
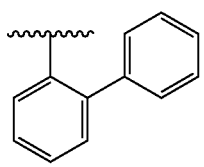
13. A compound according to claim 12, wherein A is selected from one of the following groups:
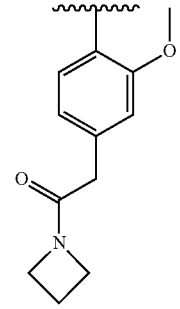
12. A compound according to claim 1, wherein A is selected from one of the following groups:
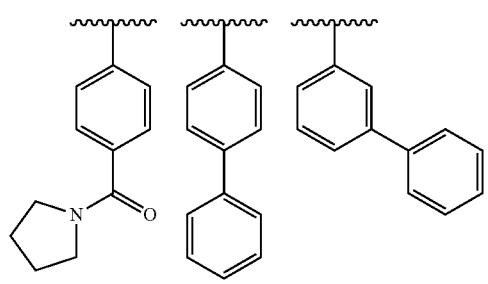
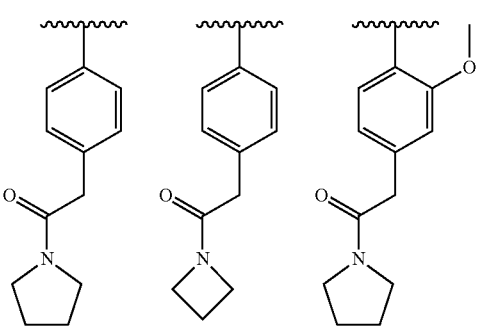
14. A compound according to claim 1, wherein A is selected from one of the following groups:
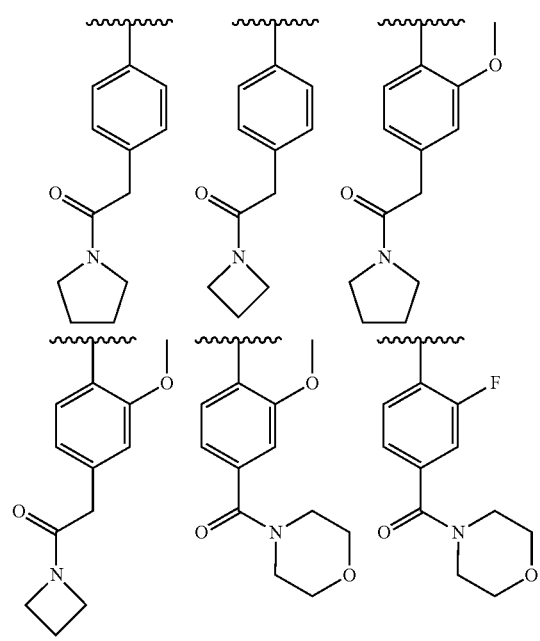
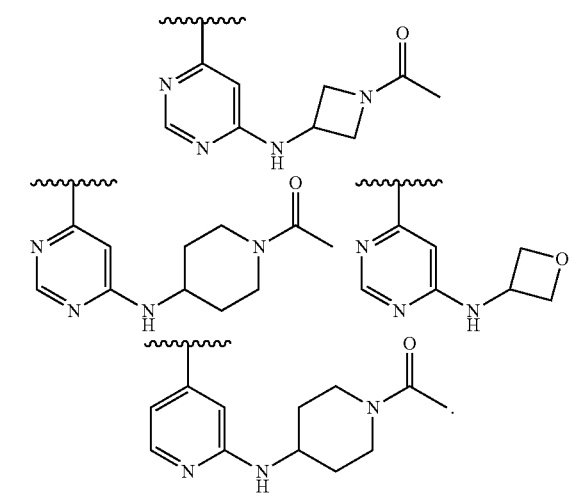

15. A compound according to claim 1, wherein A is selected from one of the following groups:

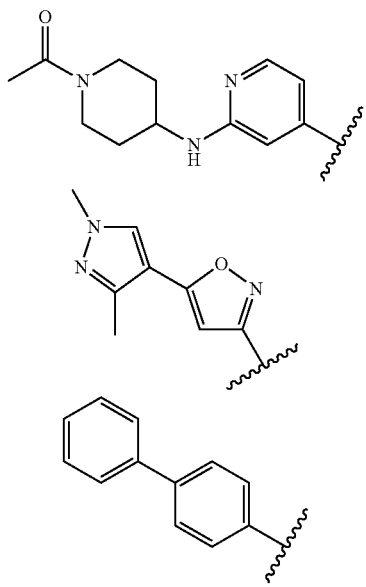

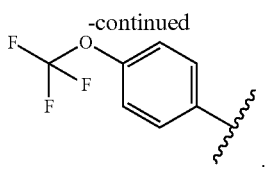

16. A pharmaceutical composition comprising a compound according to claim 1 and a pharmaceutically acceptable excipient.

17. A method of inhibiting PRMT5 in a patient in need thereof, comprising administering to the patient a PRMT5-inhibiting effective amount of a composition according to claim 16.

18. The method of claim 17, wherein said inhibition of PRMT5 treats a cancer that overexpresses PRMT5.

19. The method of claim 18, wherein said cancer is chosen from prostate cancer, lung cancer, melanoma cancer, breast cancer, colorectal cancer, gastric cancer, esophagus carcinoma, lung carcinoma, B-cell lymphoma and B-cell leukemia.

* * * * *